(12) United States Patent
Fukae et al.

(10) Patent No.: US 8,309,140 B2
(45) Date of Patent: Nov. 13, 2012

(54) EFFECT OF PORCINE SHEATH PROTEINS ON THE REGENERATION ACTIVITY OF PERIODONTAL LIGAMENT

(76) Inventors: Makoto Fukae, Tokyo (JP); Kazuhiro Gomi, Atsugi (JP); Mikimoto Kanazashi, Yokohama (JP); Shinichiro Oida, Yokohama (JP); Ayako Kakegawa, Kawasaki (JP)

( * ) Notice: Subject to any disclaimer, the term of this patent is extended or adjusted under 35 U.S.C. 154(b) by 205 days.

(21) Appl. No.: 12/763,154

(22) Filed: Apr. 19, 2010

(65) Prior Publication Data

US 2010/0227820 A1 Sep. 9, 2010

Related U.S. Application Data

(63) Continuation-in-part of application No. 11/398,885, filed on Apr. 6, 2006, now Pat. No. 7,722,900.

(60) Provisional application No. 60/669,670, filed on Apr. 9, 2005.

(51) Int. Cl.
*A61K 35/32* (2006.01)
*C07K 1/00* (2006.01)
(52) U.S. Cl. .................. 424/549; 530/300; 530/350
(58) Field of Classification Search .................. 424/549; 530/300, 350
See application file for complete search history.

(56) References Cited

U.S. PATENT DOCUMENTS 7,722,900 B2 * 5/2010 Fukae et al. .................. 424/549

OTHER PUBLICATIONS

The sequence alignment between SEQ ID No. 35 and AC Q3B861.*
The sequence alignment between SEQ ID No. 35 and AC Q3B861, (2005).

* cited by examiner

*Primary Examiner* — Tekchand Saidha
(74) *Attorney, Agent, or Firm* — Kirk Hahn

(57) ABSTRACT

The purpose of this study was to identify the periodontal regeneration factors in enamel protein shown to induce cementum- and osteo-promotive activities in vivo. The cementum regeneration (CR), a part of periodontal regeneration, was examined by using experimental cavities prepared in a buccal dehiscence dog model. The CR activity was found in the aggregate consisted of sheath proteins along with a small amount of amelogenins separated from newly formed secretory enamel. The sheath proteins were purified to be homogeneous, and examined for the alkaline phosphatase (ALP) inducing activity of human periodontal ligament (HPDL) cells. Application of 17 kDa sheath protein induced ALP activity in HPDL cells. Peptides synthesized from the sheath protein sequence also showed ALP inducing activity. The 17 kDa sheath protein has cell differentiation activity.

18 Claims, 19 Drawing Sheets

```
     1                                                         *1                                50
p: V P A F P R Q P G T P G V A S L S L E T M R Q L G S L Q G L N M L S Q Y S R F G F G K S F N S L W M
h: V P F F P Q Q S G T P G M A S L S L E T M R Q L G S L Q R L N T L S Q Y S R Y G F G K S F N S L W M
h': V P F F P Q Q S G T P G M A S L S L E T M R Q L G S L Q R L N T L S Q Y S R Y G F G K S F N S L W M
   *   *  *  *  * * * *  * * * * * * * * * * * *  * *  * * * * * *  * * * * * * * * * * * *

51                                                                                         100
p: H G L L P P H S S F Q W M R P R E H E T Q Q Y E Y S L P V H P P P L P S Q P S L Q P Q Q P G Q K P F
h: H G L L P P H S S L P W M R P R E H E T Q Q Y E Y S L P V H P P P L P S Q P S L K P Q Q P G L K P F
h': H G L L P P H S S L P W M R P R E H E T Q Q Y E Y S L P V H P P P L P S Q P S L K P Q Q P G L K P F
   * * * * * * * *   * * * * * * * * * * * * * * * * * * * * * * * * * * * * *     * * * * *    * *

101                                                       *2                                150
p: L Q P T V V T S I Q N P V Q K G V P Q P P I Y Q G H P P L Q Q V E G P M V Q Q Q V A P S E K P P E A
h: L Q S A A A T T N Q A T A L K E A L Q P P I H L G H L P L Q E G E L P L V Q Q Q V A P S D K P P K P
h': L Q S A A A T T N Q A T A L K E A L Q P P I H L G H L P L Q E G E L P L V Q Q Q V A P S D K P P K P
   * *       *   *         *    * * *    * *       * *  * *   * * * * * * * *  * * *    *

151
p: E L P G L D F A D P Q D P S - - - - - - - - - - - - - - - - - - - - - - - - - - - - - M F P I A R 170
h: E L P G V D F A D P Q G P S L P G M D F P D P Q G P S L P G L D F A D P Q G S T I F Q I A R 196
h': E L P - V D F A D P Q G P S L P G M D F P D P Q G P S L P G L D F A D P Q G S T I F Q I A R 195
   * * *     * * * * * *   * *                                                    *   * * *
```

\*1 : N-terminal side of  
      13 kDa sheath protein

\*2 : C-terminal side of  
      13 kDa and 15 kDa sheath protein

FIGURE 15

EFFECT OF PORCINE SHEATH PROTEINS ON THE REGENERATION ACTIVITY OF PERIODONTAL LIGAMENT

CROSS-REFERENCE TO RELATED APPLICATIONS

This application is a Continuation-in-Part of U.S. Nonprovisional application Ser. No. 11/398,885 filed on Apr. 6, 2006 (pending); which claims priority to U.S. Provisional Patent application Ser. No. 60/669,670 filed on Apr. 9, 2005, the contents of which are all herein incorporated by this reference in their entireties. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

REFERENCE TO A SEQUENCE LISTING, A TABLE, OR A COMPUTER PROGRAM LISTING COMPACT DISC APPENDIX

This application refers to protein sequences by SEQ ID number. These sequences are listed below and are contained in the file "fukae-CIP-bio-seq.txt" (25 KB, created on Apr. 5, 2010), which is hereby incorporated in its entirety herein.

BACKGROUND OF INVENTION

1. Field of the Invention

The present invention relates generally to the field of periodontal tissue regeneration, and particularly concerns the treatment of diseases related to periodontitis and periodontal disease. The invention provides 17 kDa sheath protein and its derived peptides, which have cementum regeneration promoting activity and are involved in periodontal regeneration and cytodifferentiation of periodontal ligament cells. Also disclosed are the methods for isolating other enamel matrix proteins, and various therapeutic methods using the compositions of the invention.

The invention provides a cementum regeneration promoting protein segment comprising an isolated, synthesized and recombinant sheath protein, polypeptide, or peptide. In certain embodiments of the present invention, the sheath protein is a porcine sheath protein. In other embodiments of the present invention the sheath protein is a human, murine, rat, bovine, sheep, monkey and every mammal sheath protein.

As used herein in the context of various of the instant compositions and methods, the term "protein" will be understood to mean a proteinaceous segment that is longer than about 150 contiguous amino acids and in most aspects comprises more than about 70% of the amino acids encoded by a gene. As used herein in the context of various of the instant compositions and methods, the term "polypeptide" will be understood to mean a proteinaceous segment that is longer than about 50 contiguous amino acids in length, and the term "peptide" will be understood to mean a proteinaceous segment that is between about 3 and about 50 contiguous amino acids in length. Thus sheath protein proteinaceous segment of varying overall length that retain signaling, regulatory and structural properties and functions are provided herein.

As used herein in the context of various of the instant compositions and methods, the term "sheath protein" or the term "sheathlin" will be understood to include wild-type, polymorphic and mutant versions of sheath protein or sheathlin sequences. Wild-type sequences are defined as the first identified sequence; polymorphic sequences are defined as naturally occurring variants of the wild type sequence that have no effect on the expression or function of the sheath protein or sheathin proteins, polypeptides, or peptides or domain thereof; and mutant sequences are defined as changes in the wild-type sequence, either naturally occurring or introduced by the hand of man, that have an effect on either the expression and/or the function of the sheath protein or sheathlin proteins, polypeptides or peptides or domains thereof. The invention thus also includes the provision of DNA segments vectors, genes and coding sequence region that encode various forms of sheath protein or sheathlin proteins, polypeptides, peptides or any fusion protein, polypeptides or peptide thereof.

As used herein in the context of various of the instant compositions and methods, the term "cementum regeneration promoting protein" will be understood to include the proteins, polypeptides and peptides containing amino acid sequences shown a cementum regeneration promoting activity in sheath protein sequences. Wild-type sequences are defined as the first identified sequence; polymorphic sequences are defined as naturally occurring variants of the wild type sequence that have no effect on the expression or function of the sheath proteins, polypeptides, or peptides or domain thereof; and mutant sequences are defined as changes in the wild-type sequence, either naturally occurring or introduced by the hand of man, that have an effect on either the expression and/or the function of the sheath proteins, polypeptides or peptides or domains thereof. The invention thus also includes the provision of DNA segments vectors, genes and coding sequence region that encode various forms of sheath proteins, polypeptides, peptides or any fusion protein, polypeptides or peptide thereof.

The sheathlin (Hu et al., 1997a) is the parent protein of sheath protein (Uchida et al., 1995) which is named as it is accumulated to the enamel sheath of immature enamel to reveal honeycomb pattern on immunohistochemical detection. The sheath protein is firstly found to be 13 kDa~17 kDa non-amelogenin protein in newly formed enamel of pig (Fukae and Tanabe, 1987a). The sheathlin is degraded at early stage of development into three peptides, 17 kDa sheath protein, 25 kDa acidic protein and Ca binding protein (Fuake and Tanabe, 1987b).

Various therapeutic methods using the compositions of the invention contains the application for not only periodontal ligament regeneration, cementum regeneration and alveolar bone regeneration against periodontal disease and periodontitis, but also implant of artificial material like tooth and replantation of extracted tooth.

Enamel sheath protein (ESP) is involved in the construction of the enamel sheath during tooth development. The 17 kDa ESP is a one-step cleavage product processed by proteolysis from the N-terminal side of sheathlin (ameloblastin/amelin), one of the porcine enamel matrix proteins. Enamel sheath protein exhibits periodontal ligament and cementum regeneration activity in a buccal dehiscence model in dogs, and promotes the cytodifferentiation of cultured human periodontal ligament (HPDL) cells. The aim of this study was to determine the peptide segment on the C-terminal side sequence of the human ESP that possesses a cytodifferentiation activity on cultured HPDL cells.

Enamel protein extracts induce osteogenesis and/or cementogenesis. Commercially available enamel protein preparations such as Emdogain are used clinically to stimulate periodontal regeneration activity. However, the molecules and the mechanisms behind the bioactivities of these complex, multicomponent enamel protein preparations are unclear. The cementum regeneration activity, which is one aspect of the periodontal ligament regeneration activity, is carried by proteins in newly formed porcine secretory stage enamel, including the 25 kDa amelogenin, 89 kDa enamelin and 17 kDa enamel sheath 5 protein (ESP).

Amelogenins are the major structural components in the secretory stage enamel matrix, in which the growth of enamel crystals occurs. Amelogenins assemble to form micelle structures, which support the elongating enamel crystal ribbons. Amelogenins are progressively degraded by the enamel proteases, Mmp-20 and Klk4 (EMSP-1). The slow degradation of amelogenin assemblies that separate the crystals provides space for the progressive thickening of the enamel crystals, which is necessary for hardening the enamel. The 89 kDa enamelin resides mainly in the enamel rod of newly formed secretory stage enamel and has high affinity for binding to the enamel crystallites. The function of enamelin is critical for proper dental enamel formation and it thus play a role in crystal formation. The 17 kDa ESP is the N-terminal cleavage product of sheathlin, which has also been called ameloblastin or amelin, and it becomes concentrated within the sheath space between enamel rods.

When these proteins are individually tested using the buccal dehiscence model in dogs, cementum regenerating activity is exhibited by 17 kDa ESP purified from newly formed secretory stage enamel, but not by the amelogenin and enamelin fractions. Significantly, 13 and 15 kDa ESPs, which are cleavage products of 17 kDa ESP lacking the C-terminal peptide, do not exhibit any cementum regeneration activity.

In cell culture systems, the alkaline phosphatase (ALP) activity is the standard marker for the cytodifferentiation of osteoblast-like cells. Various purified ESPs have been used to stimulate human periodontal ligament (HPDL) cells, which were subsequently assayed to determine their ALP activity. Only 17 kDa ESP shows cytodifferentiation activity in a cell culture system, while other lower molecular weight ESPs do not, thus suggesting that the periodontal ligament inducing activity and cytodifferentiation activity are carried by the C-terminal segment of the 17 kDa ESP that is missing from the smaller molecular weight ESPs. Synthetic peptides were synthesized that corresponded to segments of the C-terminal sequence of porcine 17 kDa ESP, and thereby showed a cytodifferentiation activity similar to the 17 kDa ESP itself when their ALP-inducing activities of HPDL cells were evaluated in a cell culture system. Peptides corresponding to this same region of human ESP were therefore synthesized to identify any peptides demonstrating cytodifferentiation activity using an HPDL cell culture system.

2. Description of Related Art

The enamel matrix proteins (enamel matrix derivatives: EMD) are used for repairing the periodontal ligament of periodontitis as one of the periodontal regeneration remedy. It is well accepted that the enamel matrix proteins have the periodontal regeneration activity (Hammarström 1997, Hammarström et al., 1997). Nevertheless, the final periodontal regeneration which gratifies patient's desires is not always accomplished. In addition there is a risk of infection of E type or unknown virus, since the extract from porcine immature enamel matrix is used for the remedy for clinical treatment, although the risk is at present avoided by heating the enamel matrix proteins before preparing the remedy. Another risk is that immunity from EMD for repeat application to the same patient is not always denied, although clinical safety of EMD is reported (Zetterstrom et al., 1997). The biggest problem is at present scarce information about periodontal regeneration promoting factor, because the enamel matrix proteins are consisted of multi components.

Enamel Matrix Proteins

There are in the enamel matrix three enamel matrix proteins and two proteolytic enzymes. The cDNA and derived amino acid sequences of these proteins and proteinases have been revealed by previous studies. In addition, two growth factors are found to be in porcine secretory enamel matrix.

The structural proteins are amelogenin, (Fukae et al., 1983; Snead et al., 1985; Shimokawa et al., 1987), enemelin (Fukae et al., 1993; Fukae et al., 1996; Hu et al., 1997b), and sheathlin (ameloblastin/amelin) (Cerny et al., 1996; Krebsbach et al., 1996; Hu et al., 1997a). In the developing enamel matrix, enamel matrix serine proteinase (EMSP) (Fukae et al., 1977; Tanabe 1983; Tanabe et al., 1996; Simmer et al., 1998) and a novel metalloproteinase (enamelysin) (Bartlett et al., 1996; Fukae et al., 1998) are cloned and characterized. It is confirmed in porcine enamel matrix the existence of osteogenetic growth factors which are bone morphogenetic factor (BMP) and transforming growth factor (TGF)-β (Suzuki et al., 2005).

Therefore, the immature enamel matrices throughout several developing stages contain a lot of amelogenin, sheathlin and enamelin derivatives. If the purification of specific protein was performed from enamel matrix protein fraction, the purification is interrupted by the causes of a lot of amelogenin gene products and their derivatives, and their aggregation nature.

Amelogenin

Amelogenins are abundant throughout the developing enamel matrix, and have an aggregation nature in solution. They aggregate to form a precipitate in neutral pH at room temperature and reversibly change their phase into the solution at lower temperature. Protein chemical analyses suggest that apparent molecular weights of 25 kDa amelogenin, one of uncleaved amelogenin polypeptides (Fukae et al., 1980; Uchida et al., 1991) is most abundant in the porcine gene products along with 27, 18 and 6.5 kDa amelogenins produced by splicing of amelogenin mRNA (Yamakoshi et al., 1994; Hu et al., 1996; Ikawa et al., 2005).

In newly formed enamel porcine 25 kDa amelogenin is converted by the cleavage of C-terminal hydrophilic domain with the action of enamelysin into 20 kDa amelogenin, and then in advanced developmental secretory enamel the 20 kDa amelogenin is splitted out into two fragments of 6 kDa and 13 kDa amelogenins by the action of the other proteinase EMSP (KLK4). The 13 kDa amelogenin is soluble in neutral solution and disappears from the system to produce the space for crystal growth during the secretory stage enamel.

Sheathlin

Sheathlin has 65 kDa molecular mass and is the parent protein of sheath protein which is named for 13~17 kDa non-amelogenin protein found firstly in porcine newly formed enamel matrix (Fukae and Tanabe 1987a; Uchida et al., 1991). Porcine sheathlin is degraded at once after its secretion from ameloblasts into three segments, 17 kDa sheath protein derived from N-terminal side, 29 kDa calcium binding protein derived from C-terminal side (Fukae and Tanabe 1987b; Murakami et al., 1997; Yamakoshi et al., 2001) and 25 kDa acidic protein derived from middle part of molecule. The sheath protein accumulates at once to in future prism sheath space (Uchida et al., 1991; Uchida et al., 1995) and is degraded into lower molecular weight of 15 kDa and 13 kDa sheath protein in advanced developing stage of secretory enamel.

Enamelin

Enamelin is a parent protein of 155 kDa with cleavage products having apparent molecular weights of 142, 89, 56, 45, 34, 32, and 25 kDa (Fukae et al., 1996; Hu et al., 1997b). In the newly formed enamel 89 kDa enamelin is mainly existed in alkaline soluble fraction. In advanced developing secretory enamel the 89 kDa enamelin is degradated into 32 kDa enamelin which is soluble in neutral solution and has affinities for fluorohydroxyapatite (Tanabe et al., 1990) and Ca ions (Yamakoshi et al., 2001).

Growth Factors

There is additional evidence that, besides enamel proteins, potent signaling molecules may be resident in enamel extracts. Recently, bone morphogenetic protein (BMP)-like activity was deduced to be in porcine enamel extracts using ST2 cells (a mouse bone marrow stromal cell line) by the action of noggin (Iwata et al., 2002), transforming growth factor beta (TGF-β)-like activity was identified using oral epithelial and fibroblastic cells (Kawase et al., 2001). The TGF-β-like activity in the enamel matrix protein increases the ALP activity of HPDL cells, promotes their cytodifferentiation, and finally induces mineralization (Nagano 2003). The relationship between the presence of these growth factor-like activities in enamel extracts and the induction of osteogenesis and cementogenesis during periodontal regeneration is unknown.

It is shown that the periodontal ligament (PDL) is regenerated in the experimental cavities of intrabony defects created on a buccal dehiscence model in monkeys after the application of porcine enamel matrix proteins (Hammarström 1997, Hammarström et al., 1997). The idea that enamel matrix proteins are involved in the formation of cementum is based on the fact that coronal acellular extrinsic fiber cementum is formed on enamel surface in a number of species (Hammarström 1997). Application of porcine enamel matrix in experimental cavities in the roots of incisors of monkeys induces formation of acellular cementum that is well attached to the dentin. It indicates the enamel matrix proteins have the potential to induce regeneration of the same type of cementum (Hammarström 1997, Hammarström et al., 1997). The enamel matrix derivatives stimulate the proliferation and differentiation of human PDL cells (Gestrelius et al., 1997) and enhance bone formation (Boyan et al., 2000). These show that enamel proteins have bioactivities such as the induction of osteogenesis and cementogenesis.

Based on these results, the enamel proteins, enamel matrix derivatives (EMD) which is commercially available as EMDOGAIN®, are used clinically for PDL regeneration of periodontitis (Heijl 1997, Heijl et al., 1997). This new treatment induces a noteworthy result which is not obtained up to that time as the effect of periodontal disease treatment. However, when the enamel proteins are used for the treatment of periodontitis, periodontal ligament regeneration is not always accomplished to the level of expected result. It indicates that the usage of enamel proteins for the treatment of periodontal disease leaves much room for improvement.

The problem remaining to be solved is the elucidation of the real form of bioactivities contained in the enamel proteins. The researchers developed the EMD expect that the bioactivities are due to the amelogenin family a major component in enamel matrix. However, this idea is denied by finding the existence of periodontal ligament in amelogenin-deficient mice (Gibson et al., 2001). In fact, the amelogenins and their derivatives separated by ammonium sulfate precipitation fractionation (Kanazashi et al., 2004) or gel filtration system (Kanazashi et al., 2006; Fukae et al., 2006) have no cementum regeneration activity by histological analyses using experimental defects created on buccal dehiscence model of dogs.

There is another approach to estimate the bioactivities such as osteoinductive activities, BMP-like activity (Iwata et al., 2002) and TGF-β-like activity (Kawase et al., 2001). The TGF-β-like activity in the enamel matrix protein increases the alkaline phosphatase (ALP) activity of human periodontal ligament (HPDL) cells, promotes their cell differentiation and finally induces the mineralization (Nagano 2003; Nagano et al., 2004). The existences of both BMP and TGF-β in porcine enamel proteins are confirmed by lucipherase reporter assays (Suzuki et al., 2005). However, it is unclear the function of these osteoinductive factors in periodontal regeneration in in vivo system, although these may contribute to the induction of osteogenesis and cementogenesis or both and biomineralization during periodontal regeneration.

It is not doubted that the EMD has the periodontal regeneration activity. However, it is too hard to separate the activity from the EMD since the EMD consists of multi components containing a lot of amelogenins and their derivatives which have aggregation nature. To avoid the obstruction by amelogenin aggregation, the usage of newly formed secretory enamel for separating the cementum regeneration promoting factor seems to be advantageous. Because it contains the smallest amount of amelogenin degradation products comparing to the other advanced developmental immature enamel. The 0.05M carbonate buffer (pH 10.8) which inhibits the aggregation of amelogenins is employed for the separation. Over 95% of whole proteins contained in immature enamel is solubilized briefly by homogenizing in this buffer (Fukae and Tanabe, 1998).

The management to avoid the degradation of periodontal regeneration activity is employed. There are at least four proteolytic activities detected in developing dental enamel matrix. They are two metalloproteinases, gelatinase and enamelysin (MMP-20) (Bartlett et al., 1996; Fukae et al., 1998), and two serine proteinases including EMSP (KLK4) (Fukae et al., 1977; Shimizu et al., 1979; Simmer et al., 1998). Enamel matrix serine proteinase and enamelysin were cloned characterized and involved in the degradation of amelogenins and non-amelogenin proteins during not only transition stage enamel but also secretory stage enamel (Tanabe et al., 1992; Tanabe et al., 1996; Fukae and Tanabe, 1998). EMSP and proEMSP found in the secretory enamel are extracted with only the neutral phosphate buffer. The extraction of neutral soluble fraction is needed to avoid the degradation of periodontal regeneration activity, since proEMSP is activated with metalloproteinases (Tanabe et al., 1996). The action of MMP-20 found in alkaline soluble fraction was inhibited by adding at once EDTA, the inhibitor of matrix metalloproteinase, after the extraction of alkaline soluble fraction.

Complete periodontal regeneration could be accomplished by first cementum regeneration (CR) along with burying of collagenous bundles and then periodontal ligament regeneration and alveolar bone regeneration, if it is reasoned by the analogy of root formation at tooth development. Therefore, the cementum regeneration is thought to be most important part in the periodontal regeneration processes. Nevertheless, since no marker protein is found in the cementum formation, the histological analysis on buccal dehiscence model of dogs are employed for cementum regeneration (CR) activity of fractionated enamel proteins. The CR capacity of individual protein fraction obtained at each separation or purification step is evaluated step by step by the regenerated cementum of eight weeks produced on the experimental intrabony defects created along the roots of the canine mandibular premolars.

When porcine enamel proteins are separated under the difference of developmental stage and examined for their CR activity, the CR activity is found in newly formed enamel rather than the advanced developmental secretory enamel. In newly formed secretory enamel, CR activity was detected in the alkaline soluble fraction, but not in the neutral soluble fraction. When the alkaline soluble fraction was separated into 4 fractions by Sephadex G-100 gel filtration, CR activity was found in the first eluted peak (fraction 1) containing the aggregate of sheath proteins along with a small amount of amelogenins and enamelins. The other peaks consisted of amelogenins and their derivatives had no CR activity.

When the fraction 1 was separated into enamelin fraction and aggregate fraction containing sheath proteins and amelogenins, the activity was found in the aggregate fraction. It is concluded the CR activity was in sheath proteins, because the amelogenin had no CR activity. And so sheath proteins were purified in dissociative condition and homogeneous protein fraction of each 13 kDa, 15 kDa and 17 kDa sheath protein was obtained. CR activity was found only in 17 kDa sheath protein. The 17 kDa sheath protein was split into 15 kDa sheath protein by the cleavage of C-terminal side peptide and the 13 kDa sheath protein was derived from the 15 kDa sheath protein by the cleavage of N-terminal side peptide. Therefore, CR activity was existed in the sequence of C-terminal side of 17 kDa sheath protein.

After CR activity was determined to be resided in the C-terminal peptide of 17 kDa sheath protein, to search the specific sequence having CR activity was examined by the detection of alkaline phosphatase inducing activity of human periodontal ligament (HPDL) cells, after application of purified enamel proteins or their peptides on cell culture system. The employment of cell culture system is handy method to link the detection of CR promoting activity, because the increase of ALP activity of HPDL cells shown their cytodifferentiation plays important function for acellular cementum formation, deduced from morphometric evaluation in the light microscope on ALP-deficient mice (Beertsen et al., 1999). In general, it is unclear whether the evaluation of ALP activity in HPDL cell culture system contributes to the induction of osteogenesis or cementogenesis. However, CR activity resided in the 17 kDa sheath protein was determined by the regenerated cementum of eight weeks produced on the experimental intrabony defects created on the canine mandibular premolars' roots. Therefore, the increase of ALP activity of HPDL cells in the cell culture system links strongly to the evaluation of CR promoting activity of 17 kDa sheath protein or peptides. It was characterized about HPDL cells on cell culture system that ALP activity of HPDL cells induced by adding 1α-25dihydroxy-Vitamin $D_3$ was increased by adding TGF-β, and decreased by adding BMP The purified porcine three sheath proteins were examined their ALP inducing activity of HPDL cells in cell culture system. ALP inducing activity was found in 17 kDa sheath protein, but scarce activity was in 13 kDa and 15 kDa sheath proteins. It indicates the cytodifferentiation activity of HPDL cells is resided in the C-terminal side peptide of 17 kDa sheath protein. And so, based on the sequence of porcine or human sheath protein, the peptides were synthesized and examined their ALP inducing activity on the cell culture system. On human synthesized peptides, SEQ ID NO: 1 and SEQ ID NO: 2 were shown dose dependently to increase ALP inducing activity of HPDL cells. Since the activities of these peptides were not inhibited by TGF-β1 inhibitor, TGF-β1 receptor was not common receptor of these peptides.

As will be appreciated by persons skilled in the art, the invention also relates to protein sequences with deduced amino acid sequences of SEQ ID NO:1 to SEQ ID NO:34 which have preferably 5% or greater identity, more preferably 10% or greater identity, more preferably 15% or greater identity, more preferably 20% or greater identity, more preferably 25% or greater identity, more preferably 30% or greater identity, more preferably 35% or greater identity, more preferably 40% or greater identity, more preferably 45% or greater identity, more preferably 50% or greater identity, more preferably 55% or greater identity, more preferably 60% or greater identity, more preferably 65% or greater identity, more preferably 70% or greater identity, more preferably 75% or greater identity, more preferably 80% or greater identity, more preferably 85% or greater identity, more preferably 90% or greater identity, more preferably 95% or greater identity, more preferably 96% or greater identity, more preferably 97% or greater identity, more preferably 98% or greater identity, and more preferably 99% or greater identity.

The present invention further provides proteins that consist essentially of the amino acid sequences provided in SEQ ID NO: 1 to SEQ ID NO: 36 and SEQ ID NO: 39 to SEQ ID NO: 44. A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in SEQ ID NO: 1 to SEQ ID NO: 36 and SEQ ID NO: 39 to SEQ ID NO: 44. A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterogeneous amino acid residues/peptide sequences. Such a protein can have a few additional amino acid residues or can comprise several hundred or more additional amino acids.

To determine the percent identity of two amino acid sequences, the sequences are aligned for optimal comparison purposes (e.g., gaps can be introduced in one or both of a first and a second amino acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues at corresponding amino acid positions are then compared. When a position in the first sequence is occupied by the same amino acid residue as the corresponding position in the second sequence, then the molecules are identical at that position (as used herein amino acid "identity" is equivalent to amino acid "homology"). The percent identity between the two sequences is a function of the number of identical positions shared by the sequences, taking into account the number of gaps, and the length of each gap, which need to be introduced for optimal alignment of the two sequences.

Some embodiments of the present inventions are described with reference to the numbered paragraphs below:

1. A protein comprising: an isolated sheath protein that is one of a derivative produced by the action of proteinase from a sheathlin (ameloblastin/amelin), one of structural enamel proteins; and is derived from amino-terminal side of the sheathlin.

2. The protein of paragraph 1, where the isolated sheath protein is mammalian.

3. The protein of paragraph 2, where the isolated mammalian sheath protein is porcine.

4. The protein of paragraph 2, where the isolated mammalian sheath protein is human.

5. The protein of paragraph 1, where amino acid sequence of the isolated sheath protein is selected from the group consisting of SEQ ID NO: 10 and SEQ ID NO: 11.

6. A method of producing an effect comprising administering the protein of paragraph 5 to a mammal.

7. The method of paragraph 6, where the mammal is a Human.

8. A method of producing an effect comprising administering the protein of SEQ ID NO: 11 to a mammal.

9. The method of paragraph 8, where the mammal is a Human.

10. A polypeptide or peptide segment characterized as: comprising a sequence region of at least about 3 contiguous amino acids that have the same sequence as about 3 contiguous amino acids of the sequence selected from the group consisting of SEQ ID NO: 12 and SEQ ID NO: 13; or comprising from 3 to about 1,000 amino acids in length that synthesizes the polypeptide segment selected from the group consisting of SEQ ID NO: 12 and SEQ ID NO: 13.

11. The polypeptide or peptide segment of paragraph 10, wherein the segment comprises a sequence region of at least 3 contiguous amino acids of the sequence selected from the group consisting of SEQ ID NO: 12 and SEQ ID NO:13.

12. The polypeptide or peptide segment of paragraph 10, wherein the segment is from about 3 to about 1,000 amino acids in length and synthesizes an amino acid segment of an artificial sequence comprising a sequence region of contiguous amino acids of the sequence selected from the group consisting of SEQ ID NO: 12 and SEQ ID NO: 13.

13. The polypeptide or peptide segment of paragraph 10, wherein the segment is from about 3 to about 1,000 amino acids in length and biosynthesizes by a recombinant protein expression system to the amino acid segment of an artificial sequence comprising a sequence region of contiguous amino acids of the sequence selected from the group consisting of SEQ ID NO: 12 and SEQ ID NO: 13.

14. A method of producing an effect comprising administering the protein of paragraph 10 to a mammal.

15. The method of paragraph 14, where the mammal is a Human.

16. A polypeptide or peptide segment characterized as: comprising a sequence region of at least about 3 contiguous amino acids that have the same sequence as about 3 contiguous amino acids of the sequence selected from the group consisting of SEQ ID NO: 24 and SEQ ID NO: 25; or comprising from 3 to about 1,000 amino acids in length that synthesizes the polypeptide segment selected from the group consisting of SEQ ID NO: 24 and SEQ ID NO: 25.

17. The polypeptide or peptide segment of paragraph 16, wherein the segment comprises a sequence region of at least 3 contiguous amino acids of the sequence selected from the group consisting of SEQ ID NO: 24 and SEQ ID NO: 25.

18 The polypeptide or peptide segment of paragraph 16, wherein the segment is from about 3 to about 1,000 amino acids in length and synthesizes an amino acid segment of an artificial sequence comprising a sequence region of contiguous amino acids of the sequence selected from the group consisting of SEQ ID NO: 24 and SEQ ID NO: 25.

19. The polypeptide or peptide segment of paragraph 16, wherein the segment is from about 3 to about 1,000 amino acids in length and biosynthesizes by a recombinant protein expression system to the amino acid segment of an artificial sequence comprising a sequence region of contiguous amino acids of the sequence selected from the group consisting of SEQ ID NO: 24 and SEQ ID NO: 25.

20. A method of producing an effect comprising administering the protein of paragraph 16 to a mammal.

21. The method of paragraph 20, where the mammal is a Human.

22. A polypeptide or peptide segment characterized as: comprising a sequence region of at least about 3 contiguous amino acids that have the same sequence as about 3 contiguous amino acids of SEQ ID NO: 9; or comprising from 3 to about 1,000 amino acids in length that synthesizes the polypeptide segment of SEQ ID NO: 9.

23. The polypeptide or peptide segment of paragraph 22, wherein the segment comprises a sequence region of at least 3 contiguous amino acids from SEQ ID NO: 9.

24. The polypeptide or peptide segment of paragraph 22, wherein the segment is from about 3 to about 1,000 amino acids in length and synthesizes an amino acid segment of an artificial sequence comprising a sequence region of contiguous amino acids from SEQ ID NO: 9.

25. The polypeptide or peptide segment of paragraph 22, wherein the segment is from about 3 to about 1,000 amino acids in length and biosynthesizes by a recombinant protein expression system an amino acid segment of an artificial sequence comprising a sequence region of contiguous amino acids from SEQ ID NO: 9.

26. A method of producing an effect comprising administering the protein of paragraph 22 to a mammal.

27. The method of paragraph 26, where the mammal is a Human.

28. A polypeptide or peptide segment characterized as comprising a sequence region selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8, SEQ ID NO: 26, SEQ ID NO: 27, SEQ ID NO: 28, SEQ ID NO: 29, SEQ ID NO: 30, SEQ ID NO: 31, and SEQ ID NO: 32.

29. A method of producing an effect comprising administering the polypeptide segment of paragraph 28 to a mammal.

30. The method of paragraph 28, where the mammal is a Human.

31. A composition comprising an isolated aggregate that comprises a sheath protein.

32. The composition of paragraph 31, where the isolated aggregate forms with sheath proteins and amelogenins in an alkaline solution.

33. The composition of paragraph 31, where the isolated aggregate resides in outer layer enamel, newly formed enamel, corresponding to approximately 30 μm thickness from the surface of secretory stage enamel of mammal.

34. The composition of paragraph 31, where the isolated aggregate is prepared from the outer layer enamel, newly formed enamel.

35. The composition of paragraph 31, where the isolated aggregate is separated using a method selected from the group consisting of gel filtration in alkaline solution, ion exchange chromatography, and ammonium sulfate fractionation.

36. A method of producing an effect comprising administering the protein of paragraph 31 to a mammal.

37. The method of paragraph 36, where the mammal is a Human.

38. A composition comprising isolated enamel proteins that comprise a sheath protein.

39. The composition of paragraph 38, where the isolated enamel proteins are prepared from the outer layer enamel, newly formed enamel, corresponding to approximately 30 μm thickness from the surface of secretory stage enamel of mammal.

40. The composition of paragraph 38, where the isolated enamel proteins are extracted by an alkaline solution after the extraction of neutral soluble proteins from the outer layer enamel, newly formed enamel.

41. A method of producing an effect comprising administering the protein of paragraph 38 to a mammal.

42. The method of paragraph 41, where the mammal is a Human.

This invention is not limited to specific polypeptides or peptides and the numerous modifications and variations therein will be apparent to those skilled in the art. It is also to be understood that the terminology used herein is for the purpose of describing specific embodiments only and is not intended to be limiting.

BRIEF DESCRIPTION OF THE DRAWINGS

The following drawings from part of the present specification and are included to further demonstrate certain aspects of the present invention. The invention may be better understood by reference to one or more of these drawings in combination with the detailed description of specific embodiments presented herein.

FIG. 15 shows Porcine and human enamel sheath protein (ESP) sequences. The shaded portion indicates the peptide results obtained from alternative splicing. Abbreviations: p, Porcine ESP sequence (SEQ ID NO: 10); h, Human ESP sequence obtained by database (SEQ ID NO: 11); and h', Human ESP sequence obtained from the odontoblast sample (SEQ ID NO: 36).

DESCRIPTION OF INVENTION

Figure 1:
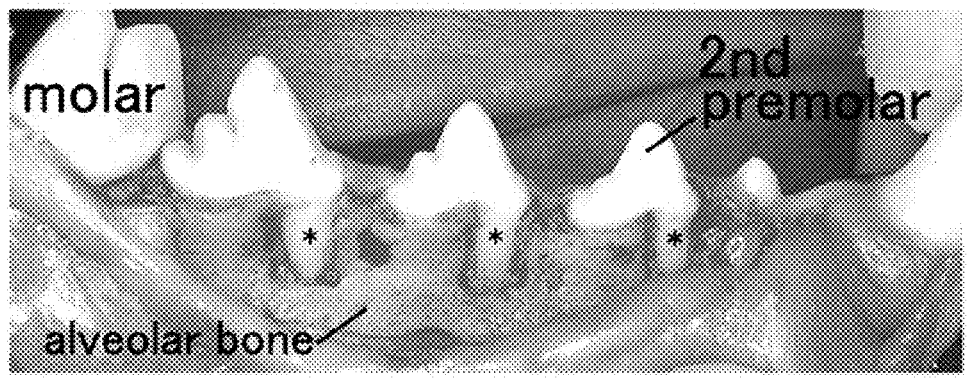
FIG. 1 is a photograph of a surgical opening for the buccal dehiscence model in the beagle mandible. Bony defects are indicated by asterisks.

Identification of Cementum Regeneration (CR) Promoting Factor in Porcine Enamel Proteins Since no marker protein is found in the cementum formation, the histological analysis on buccal dehiscence model of dogs are employed for the identification of CR promoting factor, after application of enamel proteins obtained at various purification steps. The CR promoting activity is evaluated by the regenerated cementum determined by eight-week histological analysis on one-wall intrabony defects in beagle dogs. After the determination of the protein having CR promoting activity, the sequence shown bioactivity in the protein was searched by the detection of ALP inducing activity of HPDL cells by application of purified enamel proteins or their peptides on cell culture system. Because, the ALP activity shows the cytodifferentiation of HPDL cells and plays important function for acellular cementum formation. It is deduced from morphometric evaluation in the light microscope on ALP-deficient mice (Beertsen et al., 1999). The employment of cell culture system is handy method to link the detection of cytodifferentiation activity in the enamel proteins. However, it is unclear at present whether the cytodifferentiation of HPDL cells involves in cementogenesis or osteogenesis. Therefore, if CR promoting factor was determined first, by the detection of cytodifferentiation activity of HPDL cells is useful to determine bioactive sequence in the protein shown CR promoting activity.

Regenerated Cementum Determined by Eight-Week Histological Analysis on One-Wall Intrabony Defects in Beagle Dogs Approximately 2-year-old male beagle dogs (approximate 15 kg) were used to detect the CR activities after the applications of several enamel protein samples. They had intact dentition and a healthy periodontium. The surgical preparation of buccal dehiscence type bone defects was carried out according to the modified method of Hammarström (1997) under general anesthesia induced and maintained by an endotracheal tube with 1.5-2.0% of halothane (Takeda Yakuhin Co. LTD, Osaka, Japan) in 100% oxygen, after premedicated with intramuscular injection of the mixture of Ketamine HCl (9.8 mg/kg: Sankyo Co. LTD, Tokyo, Japan) and Xylazine HCl (0.7 mg/kg: Bayer Co. LTD, Tokyo, Japan).

Contralateral buccal mucoperiosteal flaps were raised after an intracrevicular incision extending from the first mandibular premolar to the first mandibular molar. After the removing the buccal alveolar bone plate covering the mesial root of the second premolars, the exposed periodontal ligament and cementum of these areas were completely removed by means of a dental bur. At the apical end of the defect, a notch was created to identify the apical extension of the defect, when histological analyses. The distance between the cervical margin and the apical end of the defect was standardized at about 5 mm. The exposed root dentin surfaces were conditioned for 2 min with cotton pellets soaked in a 19% EDTA solution, and then carefully rinsed with sterile saline. Then 50 μg of each enamel protein sample in 100 μl of cold sterile distilled water was applied over the entire buccal surface area of the exposed roots. Finally, the mucoperiosteal flaps were repositioned to their level prior to surgery and sutured. Distilled water was used as a negative control and EMDOGAIN® (BIORA AB, Malmö, Sweden) served as a positive control.

After 8 weeks the dogs were terminated by anesthetization with sodium pentobarbital. Their heads were fixed by perfusion with 0.1 M sodium cacodylate buffer (pH 7.4) containing 4% paraformaldehyde and 1% glutaraldehyde. Tissue blocks, which included teeth, bone, and tissue were dissected and demineralized in 10% formic acid containing 0.06 M sodium citrate and 0.1 M citric acid. All specimens were dehydrated using a graded series of alcohols and then embedded in paraffin. Serial sections (5 μm thick) were made and stained with hematoxylin/eosin for examination by light microscopy.

Evaluation of Regenerated Cementum Created on the Dentin Surface

The length and thickness of cementums regenerated after application of fractionated and purified enamel protein samples and EMD were measured on the computer monitor of histological results. The length of the regenerated cementum was straight distance between the apical end of the defect and coronal extention of the new cementum, as well as to the crest of the new alveolar bone. Also, the thickness of cementum was measured at coronal end, apical end and between them. These data were statistically analyzed by t-test.

When CR promoting factor is applied to the exposed root dentin surfaces, amelogenins which have no CR activity may be useful as the carrier of CR promoting protein or peptide. Because the amelogenins aggregate each other and precipitate at 37° Centigrade in ion strength of a living body (Shimizu and Fukae, 1983), although they are dissolved in distilled water at low temperature. CR promoting protein or peptide comprise not only CR promoting factor purified from mammalian immature enamel matrix but also the synthesized peptide or recombinant protein or recombinant peptide shown CR activity.

Preparation of Newly Formed Secretory Enamel

Unless stated otherwise, all steps were carried out at 4° C. or in ice-cold conditions. Permanent incisor tooth germs are dissected from the fresh mandibles of six-month-old pigs which are purchased from the slaughter house and brought to lab in ice cold condition.

For the preparation of outer layer secretory enamel according to the method of Fukae and Shimizu (1974), permanent incisor tooth germs containing crown formation stage's developing tooth are selected. After the removal of surrounding soft tissues including pulpa, tooth is rinsed in cold saline and wiped gently with Kimwipe paper (wipers S-200) to remove excess water. On the labial side of incisor, the secretory stage enamel which is soft like cheese and translucency, distinctly different from the maturation stage's enamel of which the hardness is like chalk and collar is white. When the outermost layer beneath ameloblast cell layer of secretory enamel is prepared from the secretory stage enamel on labial side of incisor tooth germs, thin razor blade is vertically touched to the surface and moved gently and parallel to the surface. The peelings obtained by this behave corresponds approximately 30 μm depth from the surface of secretory enamel (Tanabe et al., 1992). Since the outer layer secretory enamel corresponds to the depth of approximately 30 μm from the surface of secretory enamel beneath ameloblast cell layer, it is called to be newly formed secretory enamel. One more peelings corresponded to approximately 30 μm~60 μm depth is collected to be outer-inner layer secretory enamel. This second layer was also collected since it contains the CR activity.

The inner layer sample was then scraped from the secretory enamel after the removal of a superficial layer of approximately 60 μm thickness. However, since this sample contained scarce cementum regeneration activity, it was not used for the separation of the activity. The collected samples were stored in −80° C. These preparations are based on the biochemical and histochemical evidences that the protein is most abundant in the surface of secretory enamel and decreased from the surface to enamel-dentin junction. The water, mineral and protein contents of newly formed enamel are approximately 42%, 24% and 34% per wet weight respectively.

Enamel Protein Profiles and Identification of Enamel Proteins

Protein profiles of fractionated enamel proteins were examined by acrylamide gel electrophoreses using 15% polyacrylamide slab gels containing 1% sodium dodecyl sulfate (SDS) according of the method of Laemmli (1970) and stained with Coomassie Brilliant Blue R-250. The identification of enamel proteins was carried out on Western blotting analysis using polyclonal antibodies for amelogenin, enamelin and sheath proteins (Uchida et al., 1991). After electrophoresis the gel was electro-transferred onto a GVHP membrane. The membrane was immunostained using the ABC kit and protocol (Vector Laboratoreis, USA), which employed the avidin-biotin complex method of Hsu et al., (1981).

Extraction of Porcine Enamel Proteins Containing CR Activity

Extraction of Neutral and Alkaline Soluble Fraction

The pooled samples were combined and added 20 times volume buffer per wet weight at ice cold condition. The protein in pooled sample was extracted by homogenizing for a total of 60 seconds at approximately 6,000 RPM using a Polytron homogenizer. To avoid heat up of the sample during homogenizing, 3 or 4 times interval were employed. The extraction using the same buffer was repeated 3 times. The neutral soluble fraction and alkaline soluble fraction were sequentially extracted by homogenizing in 0.05M Sörensen buffer (pH 7.4) and in 0.05M carbonate-bicarbonate buffer (pH 10.8) respectively (Fukae and Tanabe 1987a). Over 95% of total protein was extracted by these sequential extractions from the secretory enamel (Fukae and Tanabe, 1998). Approximately 16% of total proteins is solubilized in the neutral buffer and 80% is solubilized in the alkaline buffer.

When these neutral and alkaline soluble fractions separated from the newly formed enamel are examined their CR activity using buccal dehiscence model of dogs, the CR activity is found only in the alkaline soluble fraction. The residue after the alkaline buffer extraction is crystals which are bound by the crystal bound proteins although their amount is small. The crystal bound proteins are obtained by demineralization using acidic condition such as 0.5M acetic acid or EDTA solution. The composition of crystal bound proteins is quite similar to the fraction 1 separated by Sephadex G-100 gel filtration from the alkaline soluble fraction of newly formed secretory enamel (Fukae and Tanabe 1987a). Therefore it is expected that the crystal bound proteins have the CR activity.

The extraction of neutral soluble fraction could be omitted since its amount is not so big. However, neutral soluble fraction contains proenzyme of EMSP 1 (KLK4) and a small amount of active type of EMSP 1. Most of metalloproteinases are extracted in alkaline soluble fraction. To extract directly total soluble protein fraction using alkaline soluble buffer by eliminating the step of neutral soluble fraction extraction causes that it contains proenzyme of EMSP 1 which is possibly activated by the action of metalloproteinases. It is possible that CR promoting protein is degraded during its separation and purification.

Instead of homogenizing extraction, the extraction by gentle stirring could be carried out overnight at cold room in neutral and alkaline solution contained several kinds of proteinase and alkaline phosphatase inhibitors (5 mM benzamidine HCl, 2 mM 1,10-phenanthroline, 1 mM levamisole) in cold room (Fukae et al., 1996).

Each whole protein of the outer layer, outer-inner layer and inner layer enamel sample could be solubilized by demineralizing using 0.5 M acetic acid or 0.5 M EDTA solution or by denatured solution such as 4 M guanidine or 6-8 M urea in buffer. The methods using the denatured solution are disadvantage for the separation and purification of CR activity containing fraction, because the extraction contained a lot of denatured reagent. It is the biggest problem that enamel proteins consist of a lot of amelogenins and their derivatives, which have the approximate molecular weights and are characterized to have the aggregation nature.

Separation of CR Activity Containing Fraction

The alkaline soluble fraction of newly formed enamel sample was gel filtrated into 4 fractions (fraction 1-4) using a column (2.6×100 cm) of Sephadex G-100 (Pharmacia Biotech, Uppsala, Sweden), which was equilibrated with 0.05 M carbonate-bicarbonate buffer (pH 10.8). The usage of carbonate buffer due to that the alkaline condition inhibits the aggregation of amelogenins. First eluted peak (fraction 1) contained mainly 70-89 kDa enamelins, 13-17 kDa sheath proteins and a small amount of 20-25 kDa amelogenins. Second peak (fraction 2), main peak contained 20-25 kDa amelogenins. The others contained amelogenin derivatives.

The histological analysis of cementum regeneration eight weeks following application of fraction 1 and EMD showed to evaluate the cementum regenerated on dentin surface. Both samples regenerated cementum from the notch to the cervical margin. The distance from the apical end of the bone defect to the new cementum was 6.24±0.40 mm, 6.15±0.43 mm and 4.17±0.79 mm at fraction 1, EMD and control, respectively. There were significant differences between control and fraction 1 or EMD, but no significant difference between fraction 1 and EMD. Bone height from the apical end of the bone defect was 1.69±0.45 mm, 1.41±0.54 mm and 1.09±0.46 mm at fraction 1, EMD and control, respectively. Significant difference was found only between fraction 1 and control. The thickness of cementum was measured at 3 points (apical, middle, coronal) of each sample. The average thickness of cementum was 27.88±8.85 µm, 14.77±4.81 µm and 8.37±2.48 µm at fraction 1, EMD and control, respectively. Statistical significant differences were recognized between each group.

The fraction 1 induced the formation of thick acellular cementum well attached to the dentin. Numerous collagen fiber bundles arranged like in normal periodontium were produced from the regenerated cementum. The CR activity (thickness of cementum) of EMD, which was the positive control, was obviously weaker than in fraction 1. The application of water used as the negative control showed scarce CR activity.

The other fractions, which contained amelogenins and their derivatives, did not show the CR activity. This indicates that the amelogenins and their derivatives have no CR activity.

Except of Sephadex G-100 gel filtration, removal of abundant amelogenins contained in newly formed enamel could be performed by ammonium sulfate fractionation (Kanazashi et al., 2004). Most amelogenins are precipitated by approximately 6.5% saturation of ammonium sulfate in 0.05M carbonate-bicarbonate buffer (pH 10.8) in ice cold condition. The supernatant was concentrated by ultrafiltration using YM-1 membrane to use next purification step. If the aggregate of sheath protein could be fractionated by ammonium sulfate fractionation from immature secretory enamel, the method is useful to prepare the practical remedy for CR promoting since a large scale of sample is able to be prepared.

There is another method for removing abundant amelogenins from enamel proteins by the usage of their insolubility in neutral solution at high temperature.

After enamel proteins are solubilized in acidic or alkaline solution at lower temperature, the solution is neutralized by adding alkaline or acidic solution and heated to 37° C. cause the precipitation of amelogenins (Shimizu and Fukae 1983).

Separation of Aggregate Shown CR Activity

On Sephadex G-100 gel filtration of alkaline soluble fraction extracted from the outer layer sample, the first eluted peak (fraction 1) contained 70-89 kDa enamelins and the aggregate comprised of 13-17 kDa sheath proteins along with a small amount of 20-25 kDa amelogenins. In general, the larger the protein, the earlier it elutes by gel filtration chromatography. Therefore, the 13-17 kDa sheath proteins in fraction 1 form the aggregate along with a small amount of 20-25 kDa amelogenins. Because when further fractionated using a double tandem TSKgel G-3000PW column in carbonate buffer at room temperature, mostly the 13, 15, and 17 kDa sheath proteins eluted first, 70-89 kDa enamelins next, and finally the amelogenins. These small molecular weight sheath proteins likely passed through the gel filtration column as an aggregate along with a small amount of amelogenins even in alkaline condition.

The bioactive fraction 1 from the Sephadex G-100 separation contained 70-89 kDa enamelin and the aggregate of 13-17 kDa sheath proteins along with a small amount of 20-25 kDa amelogenins. If the fractions obtained by this step were examined their CR activity by histological analyses, the aggregate consists of sheath proteins shows CR activity and enamelin fraction no CR activity.

The separation of aggregate from the fraction 1 could be also separated by DEAE ion exchange HPLC column (9×100 mm) of EXPRESS-ION™ EXCHANGER Q (Whatman, Whatman International Ltd, Springfield Mill, England) equilibrated with 0.05M Tris-HCl buffer containing 6M urea (pH 7.4). The proteins were eluted with a linear NaCl gradient (0-1.2 M). The aggregate is not retarded in this column system, and pass through the column, but the enamelin retarded and eluted in higher NaCl concentration. Therefore, the aggregate consisted of 13-17 kDa sheath proteins along with a small amount of 20-25 kDa amelogenins are separated from 70-89 kDa enamelins around at neutral pH by DEAE ion exchange chromatography.

Purification of 13, 15 and 17 kDa Sheath Proteins

The fraction contained sheath proteins was further separated by gel filtration recycle system using a column (2.5×95 cm) of Cellulofine GCL-2000 (Chisso Ltd, Makuhari, Japan) or double tundem columns (7.5 mm I.D.×60 cm) of TSKgel G3000PW (TOSOH, Tokyo, Japan) equilibrated in 0.05M Tris-HCl buffer contained 4M guanidine-HCl (pH7.4). The 13, 15 and 17 kDa sheath proteins are purified by 12 times recycle system of TSKgel G3000PW column to be homogeneous.

The gel filtration by 12 times recycling of double tundem columns (7.5 mm I.D.×60 cm) of TSKgel G3000PW is as same as the gel filtration using over 28 m column of TSKgel G3000PW.

Amino Acid Sequence of 17 kDa Sheath Protein

Amino acid sequence analysis of each purified sheath proteins showed that they are derived from sheathlin the parent protein (Hu et al., 1997a). Amino acid sequence analyses were carried out using SHIMAZDU protein sequencer PPSQ-23A (Shimadzu Co., Kyoto, Japan).

Porcine 17 kDa sheath protein amino acid sequence is SEQ ID NO: 10.

The sequence of human sheath protein deduced from the human sheathlin (ameloblastin) sequence is SEQ ID NO: 11. SEQ ID NO: 36 is the sequence of a modified human sheath protein.

Characterization of Isolated 17, 15 and 13 kDa Sheath Proteins

Characterization of the isolated 17, 15, and 13 kDa sheath proteins demonstrate that the 17 and 15 kDa sheath proteins are N-terminal cleavage product of sheathlin containing 170 and 130 amino acids, respectively. The 13 kDa sheath protein contains the 99 amino acids extending from $M^{32}$ to $Q^{130}$.

Therefore, the 15 kDa sheath protein is produced by the cleavage of C-terminal 40 amino acids of 17 kDa sheath protein. The 13 kDa sheath protein is derived from the N-terminal side of 15 kDa sheath protein by splitting out 31 amino acid residues.

Identification of CR Promoting Protein in Enamel Proteins

When purified 17 kDa and 15 kDa sheath protein were tested for the histological analyses of cementum regeneration eight weeks (Kanazashi et al., 2006), the thickness of regenerated cementum after application of 17 kDa and 15 kDa sheath protein was 31.77±3.78 µm and 8.13±2.06 µm respectively. Therefore, the 17 kDa sheath protein induced a thick acellular cementum, but the 15 kDa sheath protein showed scarce CR activity.

The evidence shows that 17 kDa sheath protein is the CR promoting protein and the CR activity resides in the C-terminal side peptide of 17 kDa sheath protein, of which the peptide is not in the 15 kDa sheath protein. Porcine bioactive sequence shown CR promoting activity is SEQ ID NO: 12. Deduced human bioactive sequence is SEQ ID NO: 13.

And so, to determine the shortest bioactive sequence is examined by the detection of ALP inducing activity of HPDL cells.

Identification of Sequence Having Cytodifferentiation Activity by the Detection of Alp Inducing Activity of HPDL Cells on Cell Culture System Cell Culture of HPDL Cells and ALP Activity Assay Human periodontal ligament (HPDL) cells were obtained according to the method of Somerman et al., (1988) from healthy premolars which were extracted from the patients for orthodontic reasons. The cells were precultured for 4-6 passages with a-MEM medium to establish the primary cell line. The cells were maintained in the alpha modification of Eagle's medium (α-MEM; Life Technologies, Grand Island, N.Y., USA) containing 10% fetal bovine serum (FBS; Asahi Technoglass, Chiba, Japan) and 1% antibiotics (100 U/ml of Penicillin-G and 100 µg/ml of Streptomycin sulfate; Gibco BRL, Grand Island, N.Y., USA) at 37° C. in a humidified 5% $CO_2$ atmosphere. The ST2 cells (Riken Cell Bank, Tsukuba, Japan), an osteoblast-like mouse bone marrow stromal cell line, were cultured under the same conditions.

HPDL cells were distributed in 96-well plates at a density of approximately $5\times10^5$ cells per a well and incubated for 24 h. The growth medium was then changed to contain 10 nM of 1α-25dihydroxy-Vitamin $D_3$ (CALBIOCHEM, La Jolla, Calif.) and 50 µg/ml (final concentration) of fractionated enamel protein samples or synthesized peptides dissolved in ultrapure water. After 96 additional hours of incubation, the cells were washed once with PBS, and ALP activity was determined after a 10 min incubation at 37° C. in 10 mM p-nitrophenylphosphate (substrate) in 100 mM 2-amino-2-methyl-1,3-propanediol-HCl buffer (pH 10.0) containing 5 mM $MgCl_2$. After adding 0.2 M NaOH, which stopped the reaction, the absorbance at 405 nm was read on a plate reader. Controls included the use of recombinant growth factors (BMP-2 500 ng/ml; TECHNE Co., Minneapolis, USA, TGF-β1 50 ng/ml; R&D Systems, Inc., Minneapolis, USA).

In cell culture systems of the HPDL cells and ST2 cells, the 1α-25dihydroxy-Vitamin $D_3$ plays the important role for the induction of ALP activity of HPDL and ST2 cells. The ALP activity of HPDL cells increased by stimulation of 1α-25dihydroxy-Vitamin $D_3$ is further increased by stimulation of TGF-β1, but reduced by stimulation of BMP-2. It is shown that the HPDL cells stimulated by TGF-β1 induce the mineralization in long term cell culture (Nagano, 2003). In contrast, the ALP activity of ST2 cells is increased by stimulation of BMP-2, but is not stimulated by TGF-β1. If the ALP activity of HPDL cells were stimulated by BMP-2, it is shown that the cytodifferentiation of the cells direct to osteoblast-like cells.

Mineralization Activity

The HPDL cells were plated in 24-well plates at an initial density of $1\times10^5$ cells/well. After 24 h of incubation, the medium was replaced with growth medium containing 50 µM ascorbic acid, 10 mM β-glycerophosphate, and 10 nM 1α,25-dihydroxyvitamin $D_3$ (differentiation medium) and 1 µg/ml of samples. The medium was changed every 72 h. The cells were maintained for 30 days and then the medium was discarded.

The compartments of cells were fixed in 100% methanol, stained with alizarin red S for 10 min, then washed with ultrapure water and photographed to examine the biomineralization activity. The staining solution was 1% alizarin red S (sodium alizarin sulfonate) (Sigma) dissolved in ultrapure water and adjusted to pH 6.4 with 0.1N ammonium hydroxide.

For measuring the calcium content, the compartments of cells were dissolved by 0.5N hydrochloric acid. The resulting solution was measured by a Calcium C-test kit and protocol (Wako Pure Chemical Industries Ltd, Osaka, Japan). The absorbance at 570 nm was read on a plate reader.

Alp Inducing Activity of Purified Sheath Proteins or Synthetic Peptides Using Cell Culture of HPDL and ST2 Cells HPDL cells of approximately $5\times10^5$ cells per well were distributed in 96-well plates and incubated for 24 h. The growth medium was then changed to contain 10 nM of 1α-25dihydroxy-Vitamin $D_3$ and 50 µg/ml (final concentration) of purified sheath protein or synthesized peptide. After 96 additional hours of incubation, ALP activity was determined using p-nitrophenylphosphate as a substrate. For positive controls, the recombinant BMP-2 and TGF-β1 were added 500 ng/ml and 50 ng/ml, respectively.

Each purified sheath proteins were examined to increase the ALP activity of HPDL and ST2 cells on cell culture system. The ALP activity of the HPDL cells was enhanced by the addition of the 17 kDa sheath protein, but not by the 15 or 13 kDa sheath proteins. The sheath proteins did not enhance the ALP activity of ST2 cells, which were enhanced by adding the BMP-2. These evidences indicate that the cytodifferntiation activity resides in C-terminal side peptide of 17 kDa sheath protein, which is not contained in the 15 kDa sheath protein, since 15 kDa sheath proteins is derived from the 17 kDa sheath protein by splitting out the C-terminal side peptides. It is suggested that the cytodifferntiation activity shown by the cell culture system links strongly to CR promoting activity determined in in vitro system of buccal dehiscence model of dogs.

In some case, the application of 15 kDa sheath protein in HPDL cell culture system showed the increase of ALP inducing activity than that of 13 kDa sheath protein. It indicates N-terminal side peptide of 17 kDa sheath protein may have also the cytodifferentiation activity of HPDL cells, although its activity is small.

When 25 kDa amelogenin and amelogenin derivatives (6 kDa, 13 kDa, 20 kDa) purified from porcine immature enamel matrix were examined their ALP inducing activity of HPDL cells on the cell culture system, they have the activity like TGF-β1. The 20 kDa amelogenin is derived by splitting out C-terminal hydrophilic peptide from 25 kDa amelogenin, most abundant uncleaved amelogenin polypeptides in the porcine gene products. This degradation occurs in the outer layer secretory enamel by the action of MMP-20. The 20 kDa amelogenin is degraded into two pieces, 6 kDa and 13 kDa amelogenins by the action of EMSP1 during the advanced developmental secretory enamel. The 6 kDa amelogenin derived from N-terminal side and 13 kDa amelogenin is derived from C-terminal side of 20 kDa amelogenin. In these amelogenin and its derivatives, 6 kDa amelogenin have the strongest ALP inducing activity of HPDL cells. Moreover, N-terminal side peptide of 6 kDa amelogenin, SEQ ID NO: 6 had ALP inducing activity in synthesized peptides deduced from sequence of 6 kDa amelogenin. These indicate that amelogenin have cytodifferentiation activity of HPDL cells as same as the sheath protein. However, since amelogenins have no CR promoting activity on buccal dehiscence model of dogs, they may involve in the induction of osteogenesis during periodontal regeneration.

Amino acid sequence of porcine 6 kDa amelogenin is SEQ ID NO: 14.

Synthetic Peptides
A-1: SEQ ID NO: 15
A-2: SEQ ID NO: 16
A-3: SEQ ID NO: 17
A-1-1: SEQ ID NO: 6
A-1-2: SEQ ID NO: 7
A-1-3: SEQ ID NO: 8

The peptides synthesized based on the amino acid sequence of 6 kDa amelogenin were examined their ALP inducing activity of HPDL cells in cell culture system. Since N-terminal side peptide (A-1) showed the strong bioactivity, more shorter peptides were synthesized based on the sequence of A-1 and examined their bioactivity. The result shows that A-1-1 and A-1-2 promote ALP inducing activity of HPDL cells in cell culture system. The A-1-1 peptide promotes the bioactivity at high concentration (1 μg/ml) and the A-1-2 peptide at low concentration (10 ng/ml) in cell culture system.

It is unclear at present whether the cytodifferentiation activity of HPDL cells revealed by the increase of ALP inducing activity in cell culture system induces cementogenesis or osteogenesis. It is well accepted that osteoblasts express RANKL (ODF) to produce osteoclasts involved in bone resorption after the stimulation of 1α-25dihydroxy-Vitamin $D_3$. On the other hand, cementoblasts is not involved in cement resorption. And so, the expression of RANKL detected by using its specific antibody or its mRNA detected by RT-PCR could be useful to determine whether cytodifferentiation of HPDL cells indicated cementogenesis or osteogenesis.

Synthesized Peptides

Six peptides are synthesized as followed based on the N- and C-terminal side sequence of porcine 17 kDa sheath protein.

Their sequences are SEQ ID NO: 18 (N-1), SEQ ID NO: 19 (N-2), SEQ ID NO: 20 (N-3), SEQ ID NO: 21 (C-1), SEQ ID NO: 22 (C-2) and SEQ ID NO: 23 (C-3) respectively.

The bioactivities of the synthetic peptides were also tested using the cell culture system of HPDL and ST2 cells. When application of 50 μg/ml of the C-1 peptide, which is at the C-terminus of the 17 kDa sheath protein and not found on either the 15 or 13 kDa sheath proteins, it enhanced the ALP activity of the HPDL cells. Some of the other peptides reduced the ALP activity of HPDL cells, as did BMP-2. However, no synthesized peptide enhanced the ALP activity of ST2 cells.

In this experiment, a fault is that approximately 10 times high concentration of synthetic peptide compared with 17 kDa sheath protein was applied to detect the increase of ALP inducing activity of HPDL cells. The average molecular weight of synthetic peptides is approximately 1.6 kDa and the molecular weight of 17 kDa sheath protein is approximately 18 kDa, deduced from its amino acid composition.

It is suspected that the bioactivity of C-1 peptide induced the cytodifferentiation of HPDL cells by the application of high concentration (50 μg/ml) is not so strong.

In some case, the application of peptide synthesized based on the N-terminal side sequence of 17 kDa sheath protein in HPDL cell culture system showed the increase of ALP inducing activity, although their activity were small. It indicates N-terminal side peptide of 17 kDa sheath protein may have the cytodifferentiation activity of HPDL cells, which link to CR activity.

Human Synthetic Peptides Based on the C-Terminal Side of Human Sheath Protein

The human extra C-terminal side peptide contains 66 amino acid residues different from the 40 residues of porcine extra C-terminal peptide. And so, 5 peptides were synthesized based on the sequence of 66 amino acids.

Their sequences are SEQ ID NO: 3 (H-1), SEQ ID NO: 1 (H-2), SEQ ID NO: 2 (H-3), SEQ ID NO: 4 (H-4) and SEQ ID NO: 5 (H-5).

The bioactivities of the synthetic peptides were tested using the cell culture system of HPDL and ST2 cells. When application of around 1 ng/ml of the H-2 and H-3 peptides, they enhanced dose dependently the ALP activity of the HPDL cells. The other peptides also enhanced the ALP activity of HPDL cells, although their activities are weaker than H-2 or H-3. No synthesized peptide enhanced the ALP activity of ST2 cells.

In the case of TGF-β1, around 10 ng/ml of TGF-β1 is apt concentration for increasing ALP inducing activity of HPDL cells in cell culture system. Since average molecular weight of synthetic peptides is 1.5 kDa, adapted concentration of these peptides for increasing ALP inducing activity of HPDL cells is 0.6 nM/liter. Since the molecular weight of TGF-β1 is 25 kDa, its concentration is 0.4 nM/liter. The activity of these peptides is almost similar concentration level as that of TGF-β1, growth factor.

When TGF-β1 receptor inhibitor (SB431542) was applied into HPDL cell culture system, the ALP inducing activity of TGF-β1 was inhibited distinctly. However, ALP inducing activity increased by application of synthetic peptide was not inhibited by adding SB431542. It is suggested cytodifferentiation activity of synthetic peptides is induced via the other receptor different from TGF-β1 receptor.

The usage of synthetic peptides is due to avoid a risk of infection of E type or unknown virus, and immunity for repeat application of CR promoting protein to the same patient. Bioactive synthetic peptide having CR activity should be effective to apply for treatment of periodontal disease. The synthetic peptide deduced from human sheath protein sequence is available to treat the periodontal disease of Islam patients The outer, outer-inner and inner layer secretory enamel were prepared from the labial side of permanent incisor tooth of crown formation stage obtained from approximately 20 porcine mandibles. Each average wet weight of sample obtained one time is shown as below. Each sample was sequentially prepared from immature enamel of incisor tooth with avoiding the contamination of each other. Therefore, the sample loss at the preparation should be taken into consideration (Table 1).

TABLE 1

|  | Wet weight | protein content |
| --- | --- | --- |
| Outer enamel sample | 0.064 g (0.044 g-0.085 g) | 0.022 g |
| Outer-Inner enamel sample | 0.153 g (0.145 g-0.159 g) | 0.041 g |
| Inner enamel sample | 2.290 g (2.209 g-2.449 g) | 0.498 g |
| Total secretory stage enamel | 2.507 g | 0.561 g |

Wet weight of O+O−I/Total wet weight of secretory stage enamel=8.65% (7.0%–10.2%)
Protein content of each sample was calculated from the values in Table 1.
Protein of O+O−I/Total protein of secretory stage enamel=11.2% (9.1%–13.2%)

Proteins of O+O−I means since not only outer layer but also outer-inner layer sample contain 17 kDa sheath protein.

Fraction 1 separated by Sephadex G-100 contained the aggregate of sheath proteins was approximately 14.4% in outer plus outer-inner layer sample, which was used as previous preparation (Fukae and Tanabe, 1987).

Therefore, protein fraction contained the aggregate of sheath proteins, which corresponded to contain fraction 1 separated by Sephadex G-100 and crystal bound proteins (negligible small), is 11.2×0.151=1.69% (1.37%-1.99%) of total protein in secretory stage enamel.

On practical extraction experiment, 45 mg of fraction 1 was obtained from 2 g of the outer layer sample. Ninety nine mg of fraction 1 should be obtained theoretically from the sample by calculation. In this case the content of fraction 1 was calculated to be 0.26% (0.57% theoretically) of total protein in secretory enamel without consideration of fraction contained in outer-inner layer secretory enamel.

The aggregate fraction was obtained 12.7 mg from 45 mg of fraction 1. Therefore, the content of aggregate fraction was 0.07% (0.17% theoretically) of total protein of secretory enamel.

The content of 17 kDa sheath protein was calculated to be approximately 0.023%, (0.056% theoretically) of total protein of secretory enamel. Because 17 kDa sheath protein is contained approximately 33% from densitometric analysis on SDS acrylamide gel electrophoretic pattern of the aggregate obtained by gel filtration or ion exchange chromatography. The value was calculated on hypothesis that all proteins had the same stainabilty by CBB staining.

At Present Fraction 1 Shows the Best CR Promoting Activity on Eight-Week Histological Analysis on One-Wall Intrabony Defects in Beagle Dogs.

When fraction 1 separated by Sephadex G-100 gel filtration from the alkaline soluble extract of the porcine outer layer secretory enamel was applied to a periodontal defect in the buccal dehiscence model, complete regeneration was induced on the dentin surface. Fraction 1 induced the formation of a thick acellular cementum well-attached to dentin from the notch to the cervical margin. Abundant collagen fiber bundles, arranged like in a normal periodontium, were produced from the regenerated cementum. These results are based on the facts that the length and thickness of cementums regenerated were measured on the computer monitor of histological results and statistically analyzed by t-test.

The stronger CR activity of fraction 1 compared with EMDOGAIN® is due to the concentration of an active ingredient of EMDOGAIN®. A considerable amount of amelogenin was removed during the preparation of fraction 1 and the concentration of the 17 kDa sheath protein, which was the true bioactive component in this fraction, increased. However, the 17 kDa sheath protein induced thick acellular cementum near the apical end of the defect, but the CR was scarce near the coronal end. Epithelial downgrowth was observed sometimes. These were different from the results-of the fraction 1 application. The absence of amelogenin may cause the decrease of the scope of the cementum regeneration, and it therefore might support as a carrier the CR activity of the 17 kDa sheath protein.

To solve EMD propylene glycol alginate is used as a carrier at practical clinical application. When CR promoting protein or peptide is applied to the exposed root dentin surfaces, amelogenins, which have cytodifferentiation activity but no CR activity, may be useful for the carrier of it. Because the amelogenins dissolved in cold distilled water aggregate each other to precipitate at 37° C. in ion strength of a living body (Shimizu and Fukae, 1983) and attach to the exposed dentin surface.

Recombinant sheath protein or bioactive peptide showing CR activity could be made based on human sheathlin (ameloblastin) cDNA prepared using human odontoblasts (Nagano et al., 2003). Human odontoblasts were obtained according to the method of Oida et al., (2002) from healthy premolars which were extracted from the patients for orthodontic reasons. Fresh extracted tooth was cut down longitudinally with bone chisel and after the pulp was removed with tweezers odontoblasts remained on the predentin surface were peeled. Since the expression of amelogenin, enamelin, sheathlin, MMP-20 and KLK4 are detected in odontoblasts, total RNA was extracted with the Stratagene Total RNA Miniprep Kit and protpcol (Stratagene, La Jolla, Calif., USA).

TABLE 2

Chemical composition of outer, outer-inner, inner layer secretory enamel (wet weight %)

| | water | mineral | total protein | neutral sol. frac. | alkaline sol. frac. |
|---|---|---|---|---|---|
| Outer (0-30 μm) | 42 | 24 | 34 | 5.4 | 29 |
| outer-inner (30-60 μm) | 35 | 38 | 27 | 5.1 | 21 |
| Inner (60-300 μm) | 34 | 47 | 19 | 5.1 | 13 |

TABLE 3

Protein yields in the neutral, alkaline and acid soluble fractions of outer, outer-inner and inner layer secretory enamel (dry weight %)

| | Total protein | Neutral sol. fraction | Alkaline sol. fraction | Acid sol. fraction |
|---|---|---|---|---|
| outer | 59.3 | 9.5 (16) | 47 (80) | 3.6 (4) |
| outer-inner | 40.8 | 7.8 (19) | 31 (77) | 4.0 (4) |
| inner | 28.8 | 7.8 (27) | 20 (68) | 4.5 (5) |

Porcine 17 kDa Sheath Protein Amino Acid Sequence

| SEQ ID NO: 10 | |
|---|---|
| Sequence Size | 170 |
| Sequence Position | 1-170 |
| hydrophobic | 94 (55.29) |
| neutral | 46 (27.06) |
| hydrophilic | 30 (17.65) |
| other | 0 (0.00) |
| [hydrophobic residues] | |
| Gly(G) | 12 (7.06%) |
| Ala(A) | 6 (3.53%) |
| Val(V) | 10 (5.88%) |
| Leu(L) | 16 (9.41%) |
| Ile(I) | 3 (1.76%) |
| Met(M) | 6 (3.53%) |
| Phe(F) | 8 (4.71%) |
| Trp(W) | 2 (1.18%) |
| Pro(P) | 31 (18.24%) |
| [neutral residues] | |
| Ser(S) | 15 (8.82%) |
| Thr(T) | 5 (2.94%) |
| Asn(N) | 3 (1.76%) |
| Gln(Q) | 23 (13.53%) |
| Cys(C) | 0 (0.00%) |
| [hydrophilic residues] | |
| Asp(D) | 3 (1.76%) |
| Glu(E) | 8 (4.71%) |
| Lys(K) | 4 (2.35%) |
| His(H) | 5 (2.94%) |
| Arg(R) | 6 (3.53%) |
| Tyr(Y) | 4 (2.35%) |

-continued

| SEQ ID NO: 10 | | |
|---|---|---|
| [other residues] | | |
| Asx(B) | 0 | (0.00%) |
| Glx(Z) | 0 | (0.00%) |
| Xaa(X) | 0 | (0.00%) |

Average Molecular Weight = 18885.15
Monoisotopic Molecular Weight = 18873.5067

The Sequence of Human Sheath Protein Deduced from the Human Sheathlin (Ameloblastin) Sequence

| SEQ ID NO: 11. | | |
|---|---|---|
| Sequence Size | 196 | |
| Sequence Position | 1-196 | |
| hydrophobic | 109 (55.61) | |
| neutral | 50 (25.51) | |
| hydrophilic | 37 (18.88) | |
| other | 0 (0.00) | |
| [hydrophobic residues] | | |
| Gly(G) | 15 | (7.65%) |
| Ala(A) | 11 | (5.61%) |
| Val(V) | 5 | (2.55%) |
| Leu(L) | 26 | (13.27%) |
| Ile(I) | 3 | (1.53%) |
| Met(M) | 5 | (2.55%) |
| Phe(F) | 9 | (4.59%) |
| Trp(W) | 2 | (1.02%) |
| Pro(P) | 33 | (16.84%) |
| [neutral residues] | | |
| Ser(S) | 18 | (9.18%) |
| Thr(T) | 8 | (4.08%) |
| Asn(N) | 3 | (1.53%) |
| Gln(Q) | 21 | (10.71%) |
| Cys(C) | 0 | (0.00%) |
| [hydrophilic residues] | | |
| Asp(D) | 7 | (3.57%) |
| Glu(E) | 8 | (4.08%) |
| Lys(K) | 6 | (3.06%) |
| His(H) | 6 | (3.06%) |
| Arg(R) | 6 | (3.06%) |
| Tyr(Y) | 4 | (2.04%) |
| [other residues] | | |
| Asx(B) | 0 | (0.00%) |
| Glx(Z) | 0 | (0.00%) |
| Xaa(X) | 0 | (0.00%) |

Average Molecular Weight = 21419.96
Monoisotopic Molecular Weight = 21406.8663

Porcine Bioactive Sequence Shown CR Promoting Activity

| SEQ ID NO: 12 | |
|---|---|
| Sequence Size | 40 |
| Sequence Position | 1-40 |
| hydrophobic | 24 (60.00) |
| neutral | 7 (17.50) |
| hydrophilic | 9 (22.50) |
| other | 0 (0.00) |

Average Molecular Weight = 4347.81
Monoisotopic Molecular Weight = 4345.1035

Human Bioactive Sequence Shown CR Promoting Activity

| SEQ ID NO: 13. | |
|---|---|
| Sequence Size | 66 |
| Sequence Position | 1-66 |
| hydrophobic | 41 (62.12) |
| neutral | 12 (18.18) |
| hydrophilic | 13 (19.70) |
| other | 0 (0.00) |

Average Molecular Weight = 6935.60
Monoisotopic Molecular Weight = 6931.4326

Possible CR Promoting Activity Sequence of N-Terminal Side of Porcine 17 kDa Sheath Protein

| SEQ ID NO: 24. | |
|---|---|
| Sequence Size | 31 |
| Sequence Position | 1-31 |
| hydrophobic | 19 (61.29) |
| neutral | 9 (29.03) |
| hydrophilic | 3 (9.68) |
| other | 0 (0.00) |

Average Molecular Weight = 3222.67
Monoisotopic Molecular Weight = 3220.7022

Possible CR Promoting Activity Sequence of N-Terminal Side of Human Sheath Protein

| SEQ ID NO: 25. | |
|---|---|
| Sequence Size | 31 |
| Sequence Position | 1-31 |
| hydrophobic | 17 (54.84) |
| neutral | 11 (35.48) |
| hydrophilic | 3 (9.68) |
| other | 0 (0.00) |

Average Molecular Weight = 3391.88
Monoisotopic Molecular Weight = 3389.7220

Six Peptides are Synthesized as Followed Based on the N- and C-Terminal Side Sequence of Porcine 17 kDa Sheath Protein.
N-1: SEQ ID NO: 18
N-2: SEQ ID NO: 19
N-3: SEQ ID NO: 20
C-1: SEQ ID NO: 21
C-2: SEQ ID NO: 22
C-3: SEQ ID NO: 23

| N-1: SEQ ID NO: 18 | |
|---|---|
| Sequence Size | 13 |
| Sequence Position | 1-13 |
| hydrophobic | 10 (76.92) |
| neutral | 2 (15.38) |
| hydrophilic | 1 (7.69) |
| other | 0 (0.00) |

Average Molecular Weight = 1322.49
Monoisotopic Molecular Weight = 1321.7143

| N-2: SEQ ID NO: 19 | |
|---|---|
| Sequence Size | 13 |
| Sequence Position | 9-22 |

-continued

| | |
|---|---|
| hydrophobic | 7 (53.85) |
| neutral | 4 (30.77) |
| hydrophilic | 2 (15.38) |
| other | 0 (0.00) |

Average Molecular Weight = 1361.57
Monoisotopic Molecular Weight = 1360.7019
N-3: Sequence No. 20

| | |
|---|---|
| Sequence Size | 13 |
| Sequence Position | 19-31 |
| hydrophobic | 6 (46.15) |
| neutral | 5 (38.46) |
| hydrophilic | 2 (15.38) |
| other | 0 (0.00) |

Average Molecular Weight = 1446.64
Monoisotopic Molecular Weight = 1445.7294
C-1: SEQ ID NO: 21

| | |
|---|---|
| Sequence Size | 15 |
| Sequence Position | 132-146 |

Average Molecular Weight = 1626.82
Monoisotopic Molecular Weight = 1625.8084
C-2: SEQ ID NO: 22

| | |
|---|---|
| Sequence Size | 15 |
| Sequence Position | 144-158 |

Average Molecular Weight = 1599.72
Monoisotopic Molecular Weight = 1598.7827
C-3: SEQ ID NO: 23

| | |
|---|---|
| Sequence Size | 15 |
| Sequence Position | 156-170 |

Average Molecular Weight = 1706.88
Monoisotopic Molecular Weight = 1705.7770

Peptides Synthesized Based on the Sequence of Human Extra C-Terminal Side Peptide (66 Amino Acids).
H-1: SEQ ID NO: 3
H-2: SEQ ID NO: 1
H-3: SEQ ID NO: 2
H-4: SEQ ID NO: 4
H-5: SEQ ID NO: 5

| H-1: SEQ ID NO: 3 | |
|---|---|
| Sequence Size | 14 |
| Sequence Position | 131-144 |

Average Molecular Weight = 1494.64
Monoisotopic Molecular Weight = 1493.7725
H-2: SEQ ID NO: 1

| | |
|---|---|
| Sequence Size | 14 |
| Sequence Position | 144-157 |

Average Molecular Weight = 1525.68
Monoisotopic Molecular Weight = 1524.7824
H-3: SEQ ID NO: 2

| | |
|---|---|
| Sequence Size | 14 |
| Sequence Position | 157-170 |

Average Molecular Weight = 1478.62
Monoisotopic Molecular Weight = 1477.6546
H-4: SEQ ID NO: 4

| | |
|---|---|
| Sequence Size | 14 |
| Sequence Position | 170-183 |

Average Molecular Weight = 1486.61
Monoisotopic Molecular Weight = 1485.7138

| H-5: SEQ ID NO: 5 | |
|---|---|
| Sequence Size | 14 |
| Sequence Position | 183-196 |

Average Molecular Weight = 1550.72
Monoisotopic Molecular Weight = 1549.7889

Example 1

Material & Methods

Figure 2:
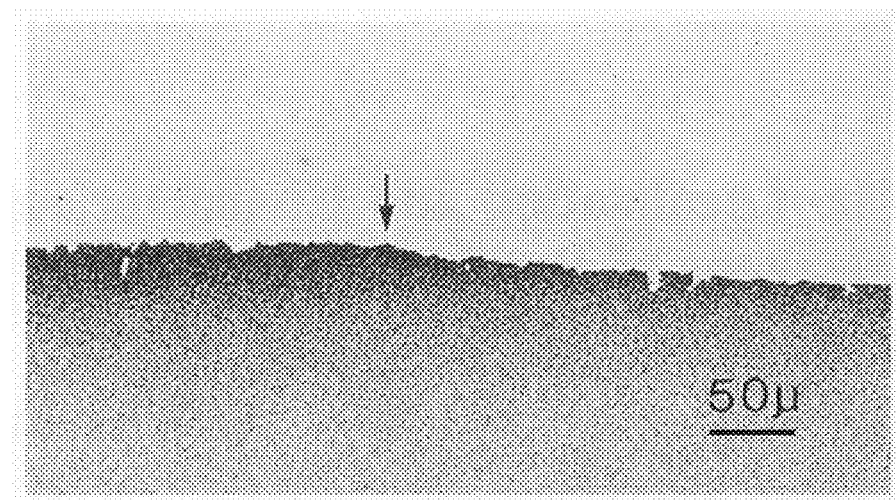
FIG. 2 is a light micrograph of the labial surface of porcine incisal secretory enamel immunostained by using carboxyl-terminal specific anti-25 kDa amelogenin. The right half of surface enamel (arrow indicates the boundary) was scraped as an outer layer secretory enamel.

All experimental procedures involving the use of animals had been reviewed and approved by the Institutional Animal Care Program of Tsurumi University.
Detection of CR Promoting Activity CR promoting activity of enamel proteins obtained at each extracted and purified step were examined by eight-week histological analysis of buccal dehiscence type bone defects created along the roots of canine mandible (FIG. 1).
Extraction of Enamel Proteins From porcine secretory enamel, the outer layer sample (newly formed enamel) and inner layer sample were prepared. From these samples, neutral soluble and alkaline soluble fractions were extracted sequentially by homogenizing in the buffer for short term. CR promoting activity was found in alkaline soluble fraction of outer layer secretory enamel. And then the CR promoting protein was separated by Sephadex G-100 gel filtration, DEAE ion exchange chromatography and finery partially purified by a gel filtration recycle system using a column of Cellulofine GCL-2000 in 4M guanidine solution.
Results The thickness of outer layer enamel was approximately 30 μm from the surface of secretory enamel (FIG. 2). Water, mineral and protein contents of outer layer secretory enamel were 42%, 24% and 34%, respectively (Table 4). Protein distribution of neutral and alkaline soluble fraction extracted from the outer layer enamel was 16% and 80% of total protein, respectively (Table 5).

TABLE 4

| | Water | Mineral | Total protein | Neutral soluble fraction | Alkaline soluble fraction |
|---|---|---|---|---|---|
| Outer (0-30 μm) | 42 | 24 | 34 | 5.4 | 29 |
| Outer - inner (30-60 μm) | 35 | 38 | 27 | 5.1 | 21 |
| Inner (60-300 μm) | 34 | 47 | 19 | 5.1 | 13 |

TABLE 5

Protein yields in the neutral, alkaline and acid soluble fractions of each enamel sample (Dry weight %)

| Sample | Total proteins | Neutral soluble fraction | Alkaline soluble fraction | Acid soluble fraction |
|---|---|---|---|---|
| Outer | 59.3 | 9.5 (16) | 47 (80) | 3.6 (4) |
| Outer-inner | 40.8 | 7.8 (19) | 31 (77) | 4.0 (4) |
| Inner | 28.8 | 7.8 (27) | 20 (68) | 4.5 (5) |

Parentheses show the protein content per total proteins

CR activity was found in the outer layer (newly formed) enamel sample rather than in the inner layer enamel sample on histological analysis on buccal dehiscence model of dogs. In the newly formed enamel sample, the CR activity was found in the alkaline soluble fraction, but not in the neutral soluble fraction.

Figure 3:
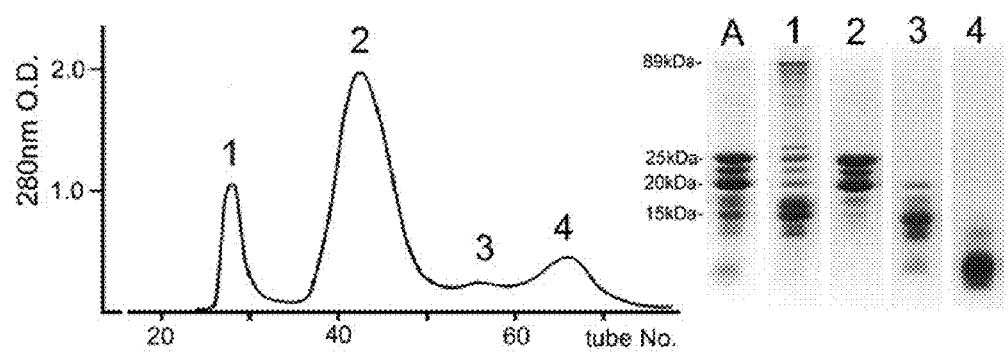
FIG. 3 is a protein profile of alkaline soluble fraction of newly formed enamel by Sephadex G-100 gel filtration and SDS-PAGE of obtained fractions. A: alkaline soluble fraction of newly formed enamel, 1: fraction 1, 2: fraction 2, 3: fraction 3, 4: fraction 4. Fraction 1 contained 13-17 kDa sheath proteins and 70-89 kDa enamelins and fraction 2 contained mainly 20 kDa-25 kDa amelogenins. Fraction 3 and 4 contained amelogenin derivatives.

The alkaline soluble fraction of newly formed enamel was separated into four fractions by Sephadex G-100 gel filtration (FIG. 3). The CR activity in these fractions was found in the first eluted peak (fraction 1), but not in the other fractions contained only amelogenins and their derivatives.

Figure 4:
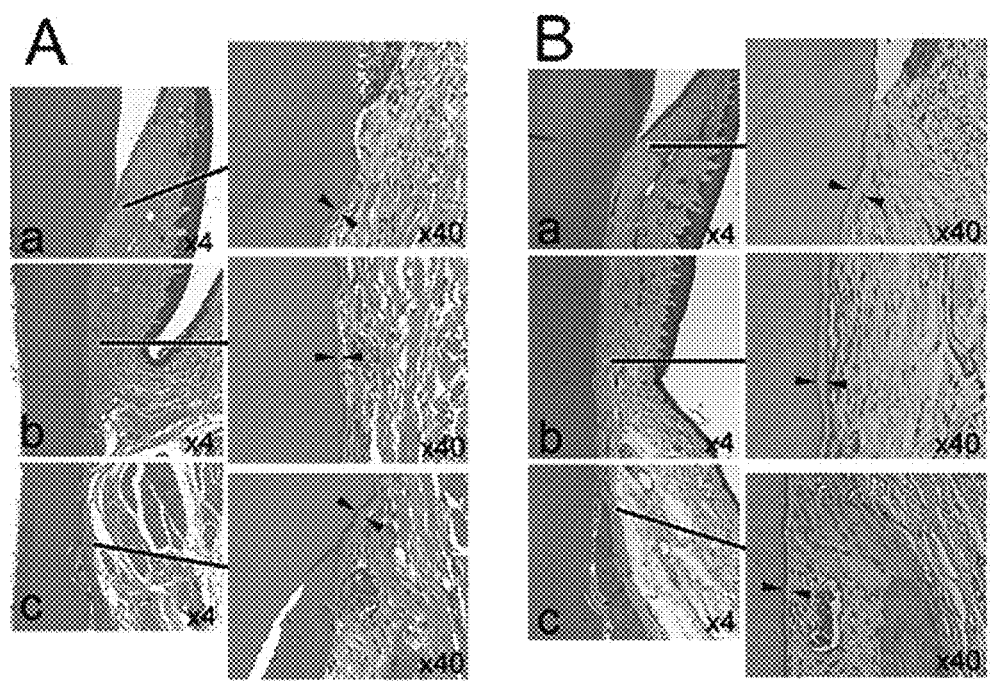
FIG. 4 is a light micrographs showing the cementum regenerated 8 weeks following the application of EMDOGAIN® (A) and the fraction 1 (B) in the experimental cavities created using the buccal dehiscence model. Key: upper part around the cervical margin (a), middle (b), bottom around the notch created to enable the identification of the apical extension of the defect (c).
Figure 5:
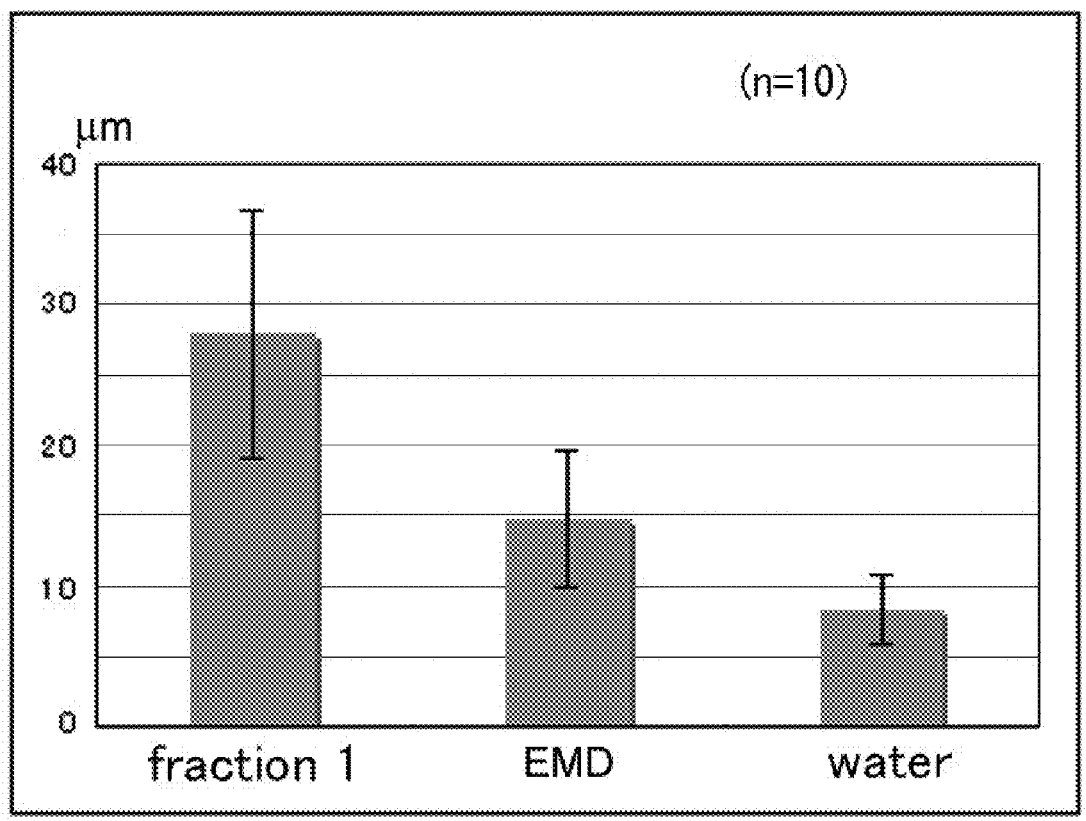
FIG. 5 is a graph showing the thickness of regenerated cementum by fraction 1, EMD and water (control). Statistically significant differences were recognized between each group (*: p<0.001).

The histological analysis of cementum regeneration eight weeks following application of fraction 1 and EMD showed both samples regenerated cementum from the notch to the cervical margin (FIG. 4). The thickness of cementum was measured at 3 points (apical, middle, coronal) of each sample. The average thickness of cementum was 27.88±8.85 µm, 14.77±4.81 µm and 8.37±2.48 µm at fraction 1, EMD and control (ddH$_2$O), respectively. Statistical significant differences were recognized between each group (FIG. 5). The fraction 1 induced the formation of thick acellular cementum well attached to the dentin. Numerous collagen fiber bundles arranged like in normal periodontium were produced from the regenerated cementum (FIG. 4-B). The CR activity (thickness of cementum) of EMD, which was the positive control, was obviously weaker than in fraction 1 (FIG. 4-A). The application of water used as the negative control showed scarce CR activity.

Figure 6:
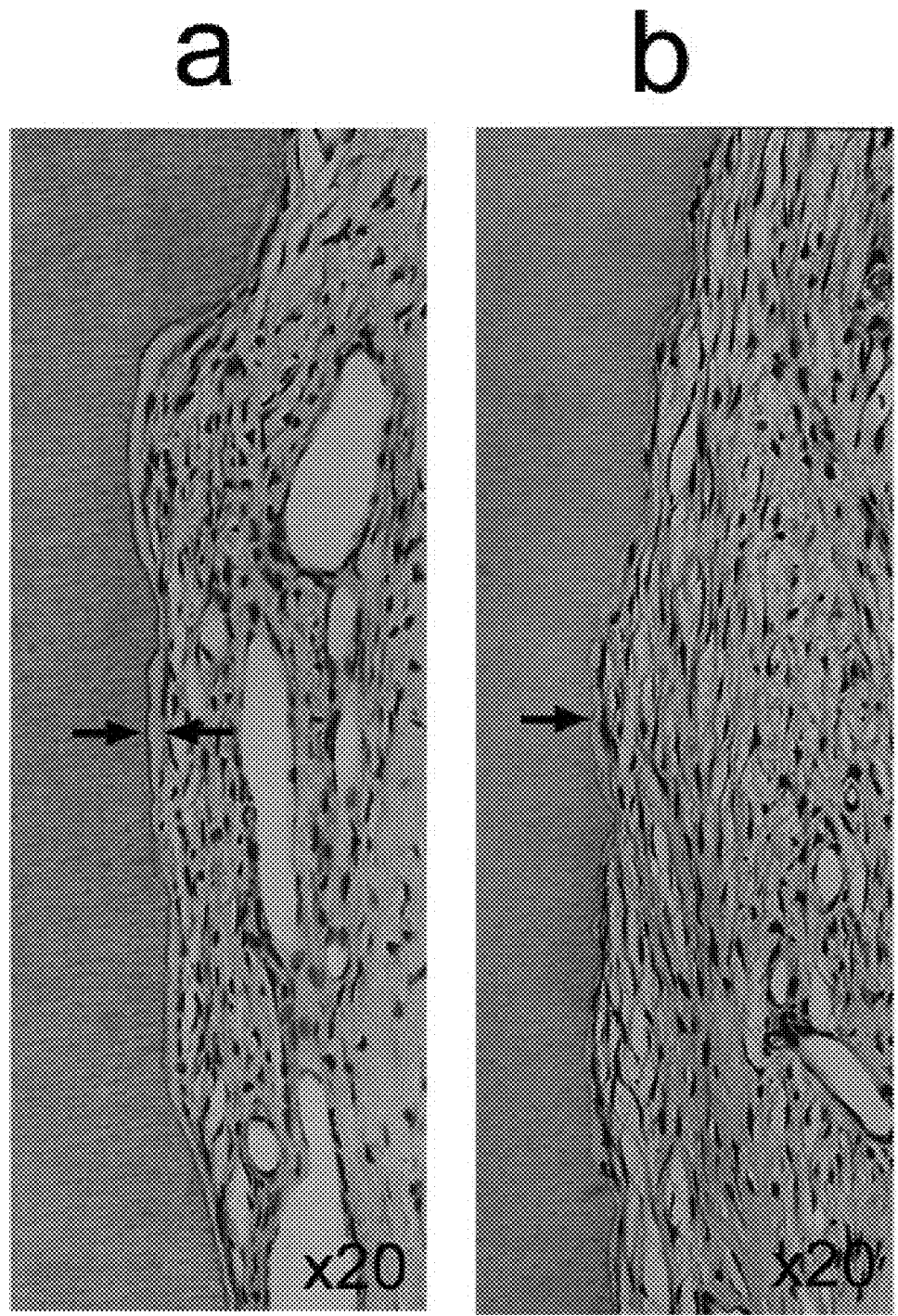
FIG. 6 is a light micrographs showing the cementum regeneration eight weeks following application of EMD (a) and fraction 2 (b) on the buccal dehiscence type bone defects created along the premolars' roots of canine mandibles FIG. 7-A: is a protein profile of fraction 1 further fractionated by DEAE ion exchange HPLC using EXPRESS-ION™ EXCHANGER Q column in 6M urea solution (pH 7.4). The sheath proteins were eluted without retard along with a small amount of amelogenins. B: Protein profile of sheath protein fraction further separated by gel filtration recycling system using a Cellulofine GCL-2000 column in 4M guanidine solution (pH 7.4). Arrows show the connection position for recycling. Arrow head shows the position connecting to fraction collector. SDS electrophoresis pattern shows the separation between 17 kDa sheath protein and 15 kDa sheath protein.

The fractions, except fraction 1, separated by Sephadex G-100 gel filtration containing amelogenins or their derivatives (fraction 2) did not show CR activity (FIG. 6-b).

It was shown on SDS electrophoreses that fraction 1 containing 70 kDa~89 kDa enamelin and 13~17 kDa sheath proteins along with a small amount of 20~25 kDa amelogenins. These sheath proteins formed the aggregate since the lower molecular weight sheath proteins were eluted at an elution position of high molecular weight protein.

Figure 7:
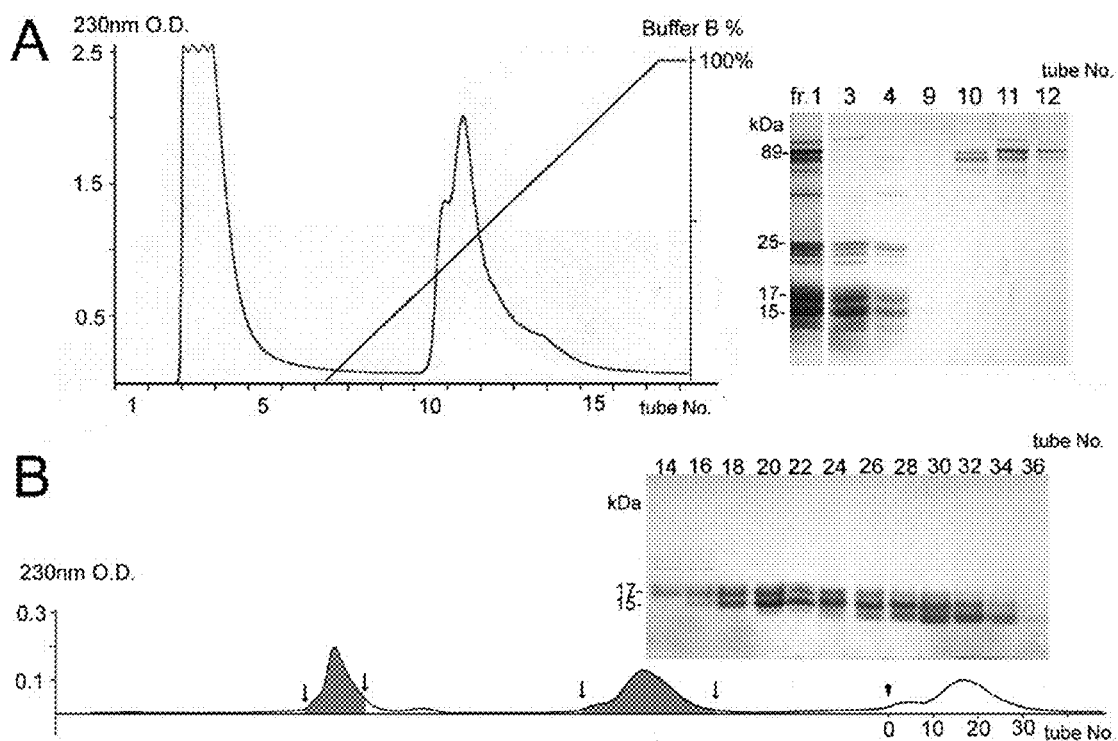

The aggregate fraction was separated from the fraction 1 by ion exchange chromatography (FIG. 7-A) and examined for its CR activity. There was CR activity in the sheath protein fraction, but not in the enamelins.

Figure 8:
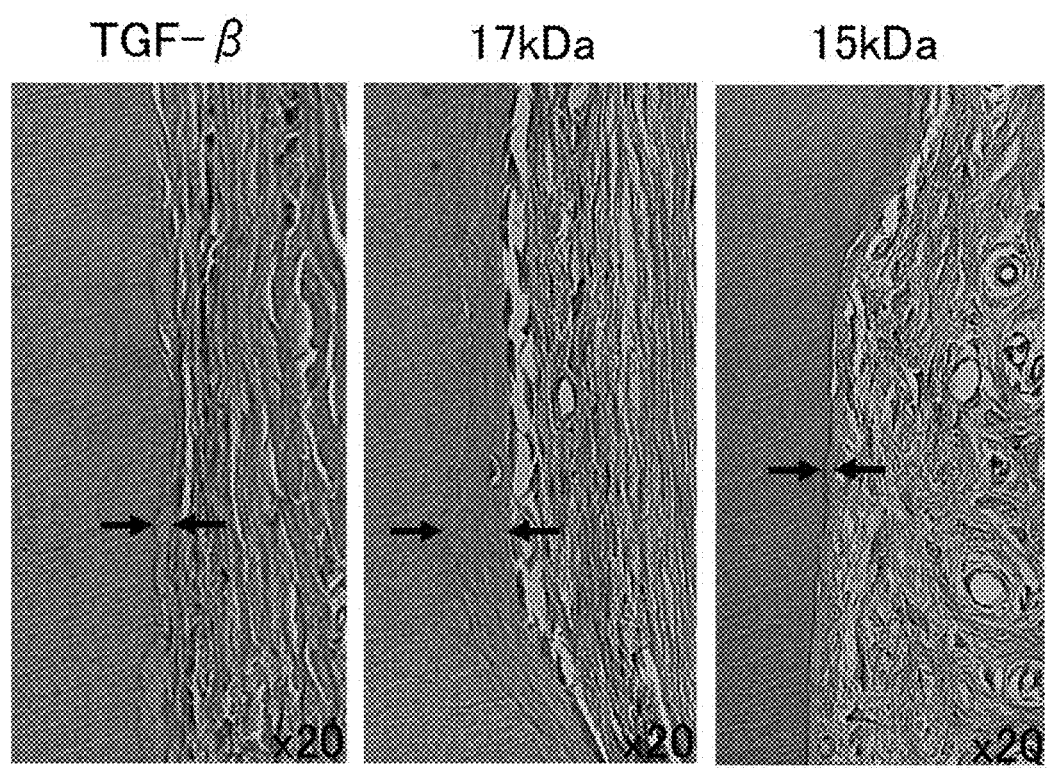
FIG. 8 is a light micrographs showing the cementum regeneration eight weeks following application of TGF-β1 (TGF-β), the 17 kDa sheath protein (17 kDa) and 15 kDa sheath protein (15 kDa) on the buccal dehiscence type bone defects created along the premolars' roots of canine mandibles
Figure 9:
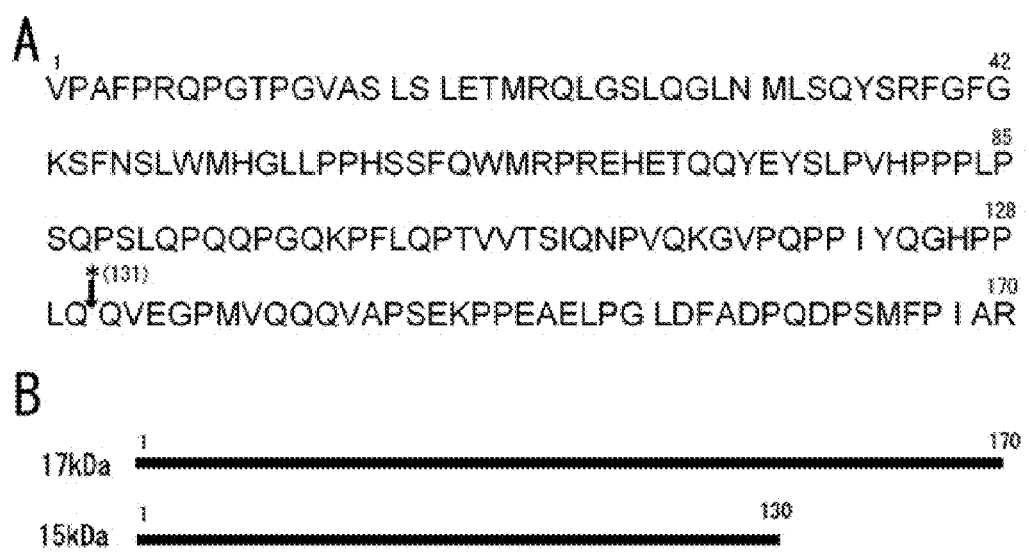
FIG. 9 is the amino acid sequence of 17 kDa sheath protein (SEQ NO. 10) (A) and the relationship of the 17 kDa (SEQ NO. 10) and 15 kDa (sequence not determined) sheath protein (B).

Partially purified 17 kDa and 15 kDa sheath proteins by gel filtration recycle system using a column of Cellulofine GCL-2000 (FIG. 7-B) were tested for their CR activity (FIG. 8). Further purified 17 kDa sheath protein induced a smaller area of cementum regeneration on the dentin surface of experimental cavities created on premolar medial roots, although the regenerated cementum was thick. The thickness of cementum was 31.77±3.78 µm and 8.13±2.06 µm with 17 kDa and 15 kDa, respectively. The 15 kDa sheath protein showed scarce CR activity. The amino acid sequence analyses of purified sheath proteins demonstrated that the 17 and 15 kDa sheath proteins corresponded to the N-terminal side of sheathlin containing 170 and 130 amino acids, respectively (FIG. 9). These indicated that the CR activity found in the 17 kDa sheath protein was located in its C-terminal side peptide, which was not found in the 15 kDa sheath protein.

Discussion

Compared with the application of EMD which showed obvious CR activity as reported previously, stronger CR activity was found reproducibly in the fraction 1 separated by Sephadex G-100 gel filtration from the alkaline soluble fraction of newly formed secretory enamel. The fraction 1 consisted of enamelins and sheath proteins formed an aggregate along with a small amount of amelogenins. It was determined from histological analysis that the 17 kDa sheath protein exhibited the CR activity, and the amelogenins and enamelins showed no CR activity.

However, further purified 17 kDa sheath protein induced a smaller area of cementum regeneration, although the regenerated cementum was thick. The result may be because water was employed for dissolution of the sample, different from the employment of propylene glycol alginate for EMD (Hammarström et al., 1997). Moreover, it is possible that this was due to the lack of amelogenins, because amelogenin may act as a carrier of CR promoting factor.

When partially purified 17 kDa and 15 kDa sheath proteins were tested for their CR activity, the 17 kDa sheath protein showed CR promoting activity, but the 15 kDa sheath protein showed scarce CR activity. Based on their amino acid sequence the 15 kDa sheath protein was derived by splitting out C-terminal side peptide from 17 kDa sheath protein. These indicated that the CR activity found in the 17 kDa sheath protein was located in its C-terminal side peptide, which was not found in the 15 kDa sheath protein. CR promoting peptide is SEQ ID NO: 12.

Example 2

Material & Methods

For the usage of human cells, informed consent was obtained from all patients under a protocol (No. 103) approved by the Ethics Committee at Tsurumi University.

Purification of Sheath Proteins

Since CR promoting activity was determined in sheath proteins which resided in newly formed secretory enamel, they were purified to be homogeneous. The aggregate of sheath proteins was separated by Sephadex G-100 Superfine gel filtration from the alkaline-soluble fraction of the outer enamel layer sample. It was further separated by HPLC using double tandem TSKgel G-3000PW columns (TOSOH, Tokyo, Japan; 7.5 mm I.D.×60 cm) in the carbonate buffer (pH 10.8). The sheath proteins in the aggregate of the first eluted peak were purified to homogeneity by recycle over the double tandem TSKgel G-3000PW columns equilibrated with 4 M guanidine solution (pH 7.4) buffer.

Six peptides were synthesized based on the amino acid sequences of N- and C-terminal side of 17 kDa sheath protein These purified sheath proteins and the peptides synthesized based on the sequence of 17 kDa sheath protein were examined their cytodifferentiation activity of HPDL cells by determination of increasing ALP inducing activity on cell culture system.

Results

Purification and Characterization of the Sheath Proteins

Figure 10:
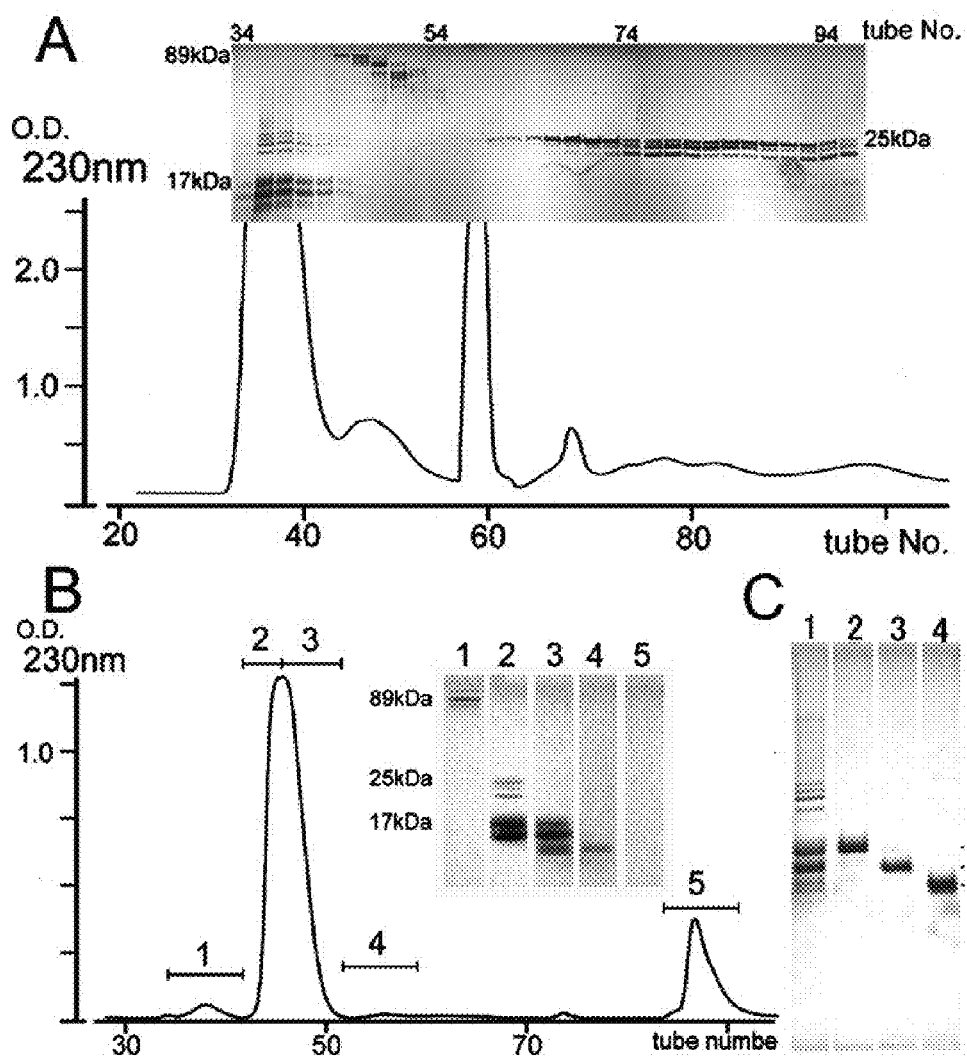
FIG. 10 is the protein profile of fraction 1 further fractionated by gel filtration HPLC using double tandem TSKgelG3000PW columns. The proteins in fraction 1 were separated using carbonate buffer (A). The first eluted peak was then separated using guanidine buffer (B). Recycling through this chromatography system purified the 17 (lane 1), 15 (lane 2) and 13 (lane 3) kDa sheath proteins to homogeneity (C).
Figure 11:
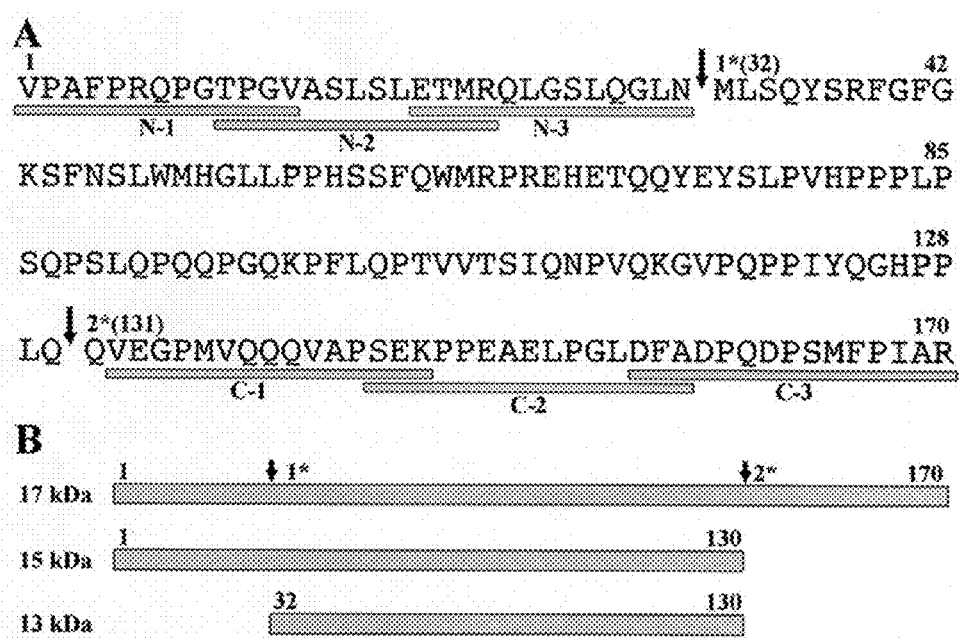
FIG. 11 is the amino acid sequence of 17 kDa sheath protein (SEQ NO. 10) (A) and the relationship of the 17 kDa sheath protein (SEQ NO. 10) and its derivatives (B). The location of the synthetic peptides N-1 (SEQ ID NO: 18), N-2 (SEQ ID NO: 19), N-3 (SEQ ID NO: 20), C-1 (SEQ ID NO: 21), C-2 (SEQ ID NO: 22), and C-3 (SEQ ID NO: 23) are indicated. *1; N-terminal end of the 13 kDa sheath protein, *2; C-terminal end of the 13 kDa and 15 kDa sheath protein. Arrows indicated cleavage sites.

The sheath proteins were purified by gel filtration recycling system using double tandem TSKgel G-3000PW columns in guanidine buffer (FIG. 10). Characterization of the isolated 17, 15, and 13-kDa sheath proteins demonstrate that the 17 and 15-kDa sheath proteins are N-terminal cleavage product of sheathlin, containing 170 and 130 amino acids, respectively. The 13-kDa sheath protein contains the 99 amino acids extending from $M^{32}$ to $Q^{130}$ (FIG. 11).

Based on N- and C-terminal side sequence of 17 kDa sheath protein six peptides were synthesized and their ALP inducing activity of HPDL cells. Their sequences are SEQ ID NO: 18 (N-1), SEQ ID NO: 19 (N-2), SEQ ID NO: 20 (N-3), SEQ ID NO: 21 (C-1), SEQ ID NO: 22 (C-2) and SEQ ID NO: 23 (C-3) respectively.

Figure 12:
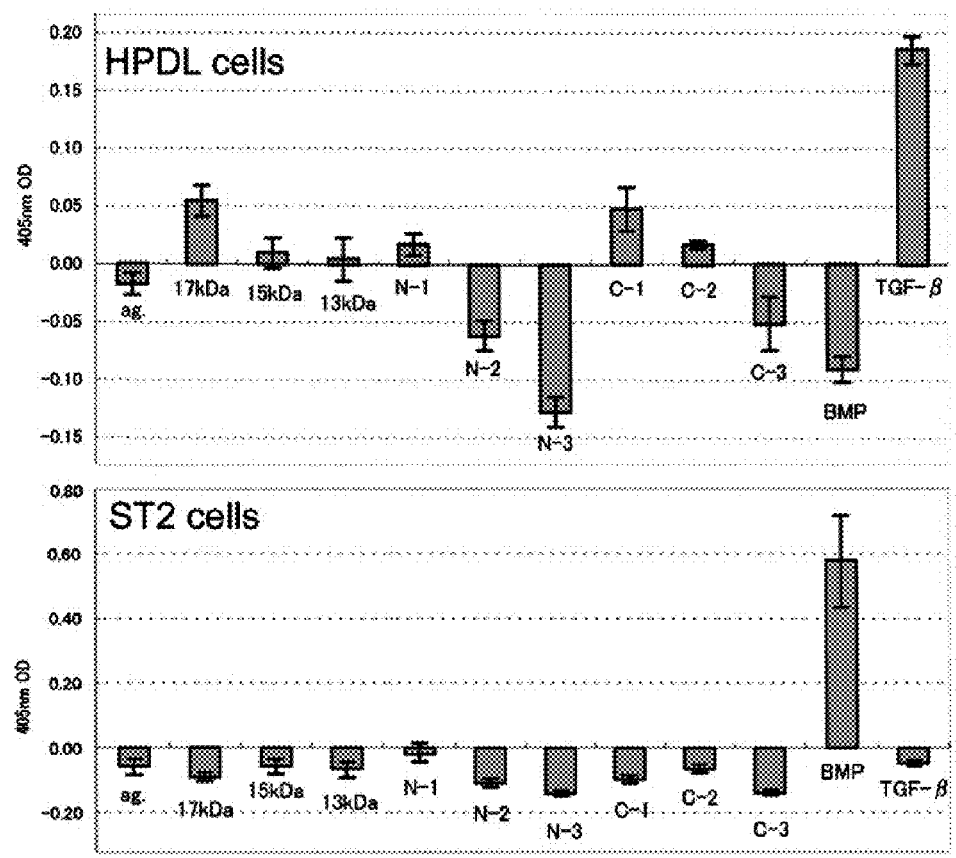
FIG. 12 shows the ALP inducing activities of HPDL cells (A) and ST2 Cells (B). Each purified sheath protein and synthetic peptide was applied at a final concentration of 50 μg/ml. The TGF-β1 and BMP-2 were applied 50 ng/ml and 500 ng/ml respectively. Data are means±SE of three culture wells. Key: ag., aggregate; 17 kDa, 17 kDa sheath protein (SEQ NO. 10); 15 kDa, 15 kDa sheath protein (sequence not determined); 13 kDa, 13 kDa sheath protein (sequence not determined); sheath protein synthetic peptides N-1 (SEQ ID NO: 18), N-2 (SEQ ID NO: 19), N-3 (SEQ ID NO: 20), C-1 (SEQ ID NO: 21), C-2 (SEQ ID NO: 22), and C-3 (SEQ ID NO: 23); bone morphogenetic protein-2, BMP-2; transforming growth factor-β1, TGF-β1.

Sheath proteins purified from the aggregate were examined for the ALP inducing activity of HPDL and ST2 cells in culture. The ALP activity of the HPDL cells was enhanced by the addition of the 17-kDa sheath protein, but not by the 15 or 13-kDa sheath proteins (FIG. 12A). The sheath proteins did not enhance the ALP activity of ST2 cells, although it was enhanced by the BMP-2 (FIG. 12B). The bioactivities of the synthetic peptides were also tested using this cell culture system. The C-1 peptide, which is at the C-terminus of the 17-kDa sheath protein and not found on either the 15 or 13-kDa sheath proteins, also enhanced the ALP activity of the HPDL cells. Some of the other peptides reduced the ALP activity of HPDL cells, as did BMP-2. However, no synthesized peptide enhanced the ALP activity of ST2 cells (FIG. 12B).

Discussion

The CR promoting protein in the porcine enamel protein was determined to be 17 kDa sheath protein using experimental bony cavities surgically created in beagle dogs. The CR activity found in the 17 kDa sheath protein was located in its C-terminal side peptide, which was not found in the 15 kDa sheath protein.

In the cell culture system, the 17-kDa sheath protein increased the ALP activity of HPDL cells. ALP activity is accepted as an indicator of cytodifferentiation from a precursor to a mineralizing cell and acellular cementum formation (Beertsen et al., 1999).

The peptide synthesized based on the amino acid sequence of the 17-kDa sheath protein also increased the ALP activity of the HPDL cells. This strongly suggests that the 17-kDa sheath protein itself induces HPDL cytodifferentiation. The C-terminal region of the 17-kDa sheath protein appears to be the true biologically active component in this fraction. The cytodifferentiation activity of this peptide links to CR activity in the experimental bony cavities created along the roots of the canine teeth.

Example 3

Material & Methods

The peptides were synthesized based on the sequence of C-terminal side peptide of human sheath protein contains 66 amino acid residues different from the 40 residues of porcine extra C-terminal peptide.

Their sequences are SEQ ID NO: 3 (H-1), SEQ ID NO: 1 (H-2), SEQ ID NO: 2 (H-3), SEQ ID NO: 4 (H-4) and SEQ ID NO: 5 (H-5). For searching the shortest peptide had cytodifferetiation activity of HPDL cells, SEQ ID NO: 26 (H-2-1), SEQ ID NO: 27 (H-3-1), SEQ ID NO: 28 (H-2-2), SEQ ID NO: 29 (H-3-2), SEQ ID NO: 30 (H-2-3), SEQ ID NO: 31 (H-3-3) and SEQ ID NO: 32 (H-2-4) were synthesized.

The bioactivities of these synthetic peptides were tested their cytodifferentiation activity of HPDL cells and ST2 cells by determination of increasing ALP inducing activity on cell culture system. When these peptides applied in cell culture system, the concentration of their peptides was employed around 1 ng/ml. In the case of TGF-1, the concentration was 10 ng/ml.

Mineralization Activity

The HPDL cells were plated in 24-well plates at an initial density of $1 \times 10^5$ cells/well. After 24 h of incubation, the medium was replaced with growth medium containing 50 µM ascorbic acid, 10 mM β-glycerophosphate, and 10 nM 1α,25-dihydroxyvitamin $D_3$ (differentiation medium) and 1 µg/ml of samples. The medium was changed every 72 h and the cells were maintained for 30 days. The biomineralization activity was examined by staining with alizarin red S and measuring calcium content.

Results

Figure 13:
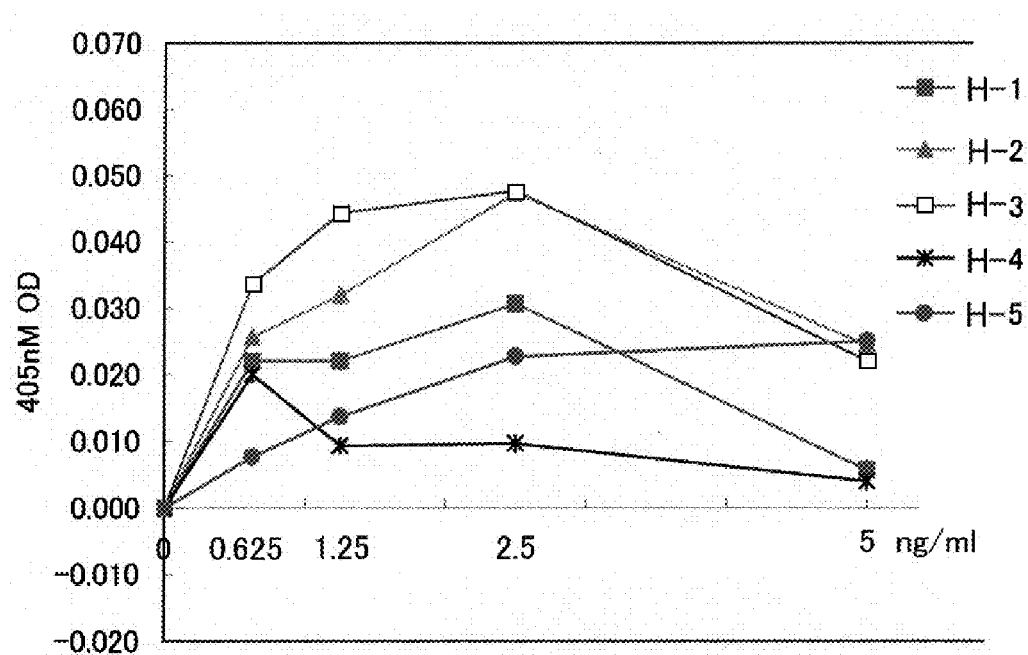
FIG. 13 shows ALP inducing activities of HPDL cells of synthetic human peptides. H-1: SEQ ID NO: 3, H-2: SEQ ID NO: 1, H-3: SEQ ID NO: 2, H-4: SEQ ID NO: 4; and H-5: SEQ ID NO: 5.

When application of around 1 ng/ml of the H-2 and H-3 peptides, they enhanced dose dependently the ALP activity of the HPDL cells (FIG. 13). The applications of these peptides enhanced the induction of mineralization of HPDL cells in in vitro cell culture system for 30 days although their mineralization levels were lower than that of TGF-β1 application. The other peptides also enhanced the ALP activity of HPDL cells, although their activities are weaker than H-2 or H-3. No synthesized peptide enhanced the ALP activity of ST2 cells. All peptides synthesized based on the sequences of H-2 and H-3 peptides increased ALP inducing activity of HPDL cells. It was confirmed LPG sequence was the shortest bioactive peptide enhanced cytodifferentiation of HPDL cells.

Figure 14:
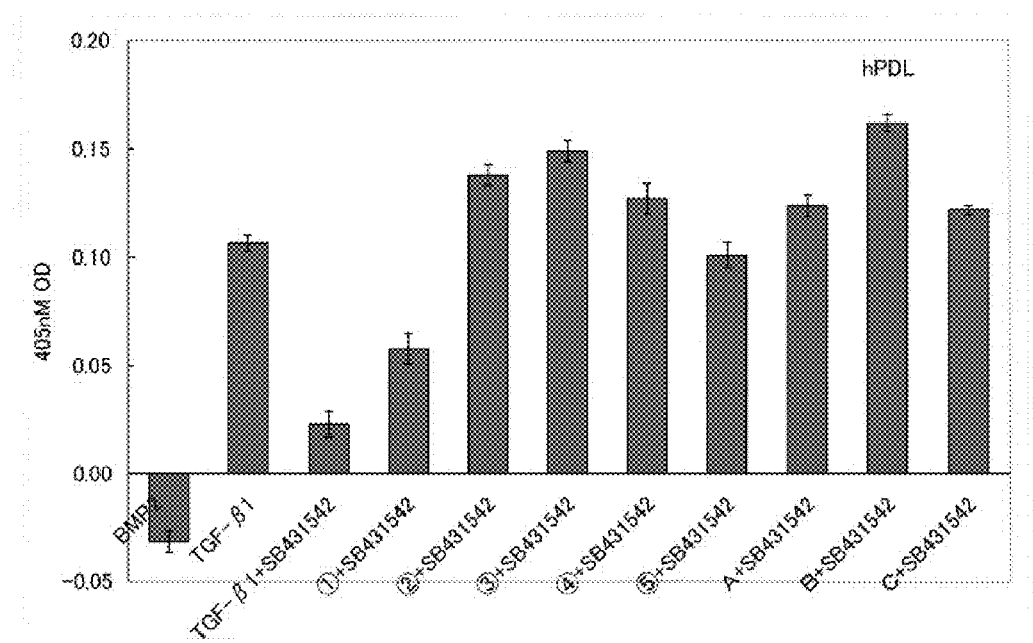
FIG. 14 shows ALP inducing activities of HPDL cells of synthetic human peptides when adding TGF-β1 inhibitor (SB431542). 1: SEQ ID NO: 3, 2: SEQ ID NO: 1, 3: SEQ ID NO: 2, 4: SEQ ID NO: 4, 5: SEQ ID NO: 5, A: SEQ ID NO: 6, B: SEQ ID NO: 7, C: SEQ ID NO: 8. A, B and C were synthesized based on SEQ ID NO: 9, the N-terminal side sequence of porcine 6 kDa amelogenin

When TGF-β1 receptor inhibitor (SB431542) was applied into HPDL cell culture system, the ALP inducing activity of TGF-β1 was inhibited distinctly. However, ALP inducing activity increased by application of synthetic peptide was not inhibited by adding SB431542 (FIG. 14). It is suggested cytodifferentiation activity of synthetic peptides is induced via the other receptor different from TGF-β1 receptor.

Discussion

The apt concentration of TGF-β1 for increasing ALP inducing activity of HPDL cells in cell culture system is around 10 ng/ml. Since the molecular weight of TGF-β1 is 25 kDa, its concentration is 0.4 nM/liter. Since average molecular weight of synthetic peptides is 1.5 kDa, adapted concentration of these peptides for increasing ALP inducing activity of HPDL cells is 0.6 nM/liter. From these concentrations in cell culture system, the activity of these peptides is almost similar concentration level as that of TGF-β1, growth factor.

When TGF-β1 receptor inhibitor (SB431542) was applied into HPDL cell culture system, the ALP inducing activity of TGF-β1 was inhibited distinctly. However, ALP inducing activity of HPDL cells increased by application of synthetic peptide was not inhibited by adding SB431542. It is suggested cytodifferentiation activity of synthetic peptides is induced via the other receptor different from TGF-β1 receptor.

It is found that some of peptides derived from the C-terminal side of human sheath protein promote the cytodifferentiation of HPDL cells to induce mineralization, which links to CR promoting activity. It is also found the shortest peptide in bioactive peptides is LPG, amino acid triplet.

Porcine enamel matrix proteins have been used already as EMDOGAIN® for clinical treatment of periodontal disease and periodontitis. At present, this remedy was preheated to avoid infection of E type virus. The treatment invalids the action of proteinases in the remedy and results to protect its CR promoting activity.

As shown in example 1, a considerable amount of amelogenin during the preparation of fraction 1 causes the concentration of an active ingredient contained in EMDOGAIN®. The removal of abundant amelogenin from EMDOGAIN® involves in the improvement of present remedy.

The methods of removal of amelogenins from enamel proteins are gel filtration in alkaline solution, ammonium sulfate fractionation and usage of insolubility of amelogenin in neutral solution at over room temperature. Therefore, the methods of removing the amelogenin from enamel proteins are included in this invention.

Although we found CR promoting protein was 17 kDa sheath protein, at present, the fraction 1 separated by Sephadex G-100 gel filtration from alkaline soluble fraction of newly formed secretory enamel showed the best CR promoting activity From example 3, the peptide contained LPG amino acid triplet will be useful to regenerate periodontal ligament which is destroyed by periodontal disease or periodontitis. The remedy for treating periodontal disease may be constructed with the peptide contained SEQ ID NO: 32, SEQ ID NO: 6 and/or SEQ ID NO: 7 (N-terminal side peptide of amelogenin) and 1α, 25-dihydroxyvitamin $D_3$. These peptide will be synthesized or made by recombinant.

Example 4

Material and Methods

The peptides synthesized on the basis of human ESP C-terminal side sequence were tested for their ability to increase the alkaline phosphatase (ALP) and mineralization activity of cultured HPDL cells. The 3 expressions of osteocalcin, osteopontin and bone sialoprotein were measured by semi-quantitative PCR and therefore were determined to be specific indicators of mineralized tissue differentiation.
Determination of the Human ESP Sequence The extracted teeth were cleaned with tissue paper and cut longitudinally by cracking with a bone chisel and dental bar into two pieces to reveal the pulp cavity. After the pulp was removed, the odontoblast cell layer on the predentin surface was directly suspended in RNA sol in order to obtain total RNA. Cloned DNA was synthesized with Ready-To-Go You-Prime First-Strand Beads. PCR primer sets for human enamel sheath protein were designed using the nucleotide sequence in the GenBank database. The two primer-pairs used were 5' TGAAGGACCTGATACTGATCC (SEQ ID NO: 37) and 5'-TGATTTGCTCCAAAAGGCACG (SEQ ID NO: 38), which generates a 718 bp amplification product.
Synthetic Peptides Several peptides were synthesized based on the sequence of the C-terminal side peptide of human and porcine ESPs. Their sequences are shown in Table 6. The P-1 peptide was used as a control because it was shown in a previous study to possess the highest ALP inducing activity among all the porcine ESP synthetic peptides tested.
Cell Cultures of HPDL Cells Normal human periodontal ligament fibroblasts were maintained in an α-minimal essential medium (α-MEM) containing 10% fetal bovine serum, either with or without 10 nM 1α-25dihydroxy-vitamin $D_3$ and 1% antibiotics (100 U/mL of penicillin G and 100 μg/mL of streptomycin sulfate) at 37° C. in a humidified atmosphere of air containing 5% $CO_2$. Another cell line, ST2 cells, was obtained from an osteoblast-like mouse bone marrow stromal cell line. These cells were cultured in the same conditions as those described above.

TABLE 6

The peptides synthesized on the basis of the human C-terminal extra peptide sequence

| | |
|---|---|
| H-1 (SEQ ID NO: 3) | EGELPLVQQQVAPS |
| H-2 (SEQ ID NO: 1) | SDKPPKPELPGVDF |
| H-3 (SEQ ID NO: 2) | FADPQGPSLPGMDF |
| H-4 (SEQ ID NO: 4) | FPDPQGPSLPGLDF |

TABLE 6-continued

The peptides synthesized on the basis of the human C-terminal extra peptide sequence

| | |
|---|---|
| H-5 (SEQ ID NO: 5) | FADPQGSTIFQIAR |
| H-2' (SEQ ID NO: 35) | SDKPPKPELPVDF |
| H-2a (SEQ ID NO: 39) | SDKPPKPELP |
| H-2b (SEQ ID NO: 40) | SDKPPKPEL |
| H-2c (SEQ ID NO: 41) | KPPKPELPVDF |
| H-2d (SEQ ID NO: 42) | VAPSDKPPKP |
| H-2e (SEQ ID NO: 43) | PELPGVDF |
| P-1 (SEQ ID NO: 44) | QVEGPMVQQQVAPSEK |

Alkaline Phosphatase Activity Assay

The ALP inducing activities of synthetic peptides using the cell culture of HPDL cells and ST2 cells were examined. The HPDL cells were distributed in 96-well plates at a density of approximately $5\times10^5$ cells per well and incubated for 24 h. The medium was then changed to α-MEM containing 10 nM of 1α-25dihydroxy-vitamin $D_3$ and either synthetic peptides or growth factors dissolved in ultra-pure water. After 96 h of incubation, the cells were washed once with phosphate-buffered saline, and 10 mM ρ-nitrophenylphosphate in 100 mM 2-amino-2-methel-1,3-propanediol-HCl buffer (pH 10.0) containing 5 mM $MgCl_2$ was added. The ALP activity was determined after 10 min incubation at 37° C. and the absorbance at 405 nm was read using a plate reader, after adding 0.2 M NaOH to stop the reaction. Positive controls included the use of recombinant growth factors, BMP-2 (1 μg/mL) and transforming growth factor-β1 (TGF-β1, 0.5 or 1 ng/mL). When the synthetic peptides were applied in the cell culture system, their final concentrations were 25 or 50 μg/mL. A TGF-β1 receptor inhibitor (SB431542, 10 μM) was applied to the HPDL cell culture system to examine their influence relative to the ALP inducing activity of the synthetic peptides.
Semi-Quantitative PCR with the Lightcycler Instrument Total RNA was extracted using RNAzol™ B from cultured HPDL cells. The cDNA was synthesized from 3 μg of the total RNA obtained from HPDL cells cultured for 4 or 21 d using an oligo-dT primer and the You-primed First-Strand Beads kit according to the manufacturer's protocol. The PCR primers were designed based upon the *Homo sapiens* mRNA sequences. The primer pairs were as follows: osteopontin, 5'-TGACCTCTGTGAAAACAGCGT-3' (SEQ ID NO: 45) and 5'-TGTACATTGTGAAGCTG TGAA-3' (SEQ ID NO: 46) (301 bp); osteocalcin, 5'-TTGTGTCCAAGCAG-GAGGGCA-3' (SEQ ID NO: 47) and 5'-ACATCCAT-AGGGCTGG GAGGT-3' (SEQ ID NO: 48) (304 bp); and bone sialo protein, 5'-GCAGAAGTGGATGAAAACGA-3' (SEQ ID NO: 49) and 5'-TGGTGGTAGTATTCTGACCA-3' (SEQ ID NO: 50) (448 bp). A primer set amplifying glyceraldehyde-3phosphate dehydrogenase mRNA was used as a control.

The cDNAs generated from HPDL cells means of the DNA Master SYBR Green I kit and protocol and a LightCycler instrument. The relative amount of each mRNA was determined at 50% levels of PCR product, and normalized with use of the relative amount of GAPDH mRNA.

Mineralization Activity

The HPDL cells were plated in six-well plates at an initial density of $1\times10^5$ cells per well. After 24 h of incubation, the medium was replaced with growth medium containing 50 µM ascorbic acid, 10 mM β-glycerophosphate and 10 nM 1α-25dihydroxy-vitamin $D_3$ (differentiation medium) and 25 µg/mL of samples. The medium was changed every 72 h. The cells were maintained for 28 d and the medium was discarded to examine the biomineralization activity by Alizarin Red S staining and also to measure the calcium content.

Analytical Methods

For Alizarin Red S staining, the compartments of 28 d cultured cells were fixed in 100% methanol, stained with Alizarin Red S for 10 min, then washed with ultra-pure water and photographed. The Alizarin Red S staining solution was 1% Alizarin Red S (sodium alizarin sulfonate) dissolved in ultra-pure water and adjusted to pH 6.4 with 0.1 N ammonium hydroxide. To measure the calcium content, the cell compartments were dissolved with 0.5 N hydrochloric acid. The resulting solution was measured using a Calcium C-test kit and protocol. The absorbance at 570 nm was read with a plate reader. The DNA sequencing of cDNA corresponding to the human enamel sheath protein was carried out using an ALF DNA zSequencer.

Statistical Analysis

All values are represented as the means±SEM. Statistical significance was determined using Student's unpaired t-test, and $p<0.05$ was considered to be statistically significant.

Results

FIG. 15 shows the amino acid sequence of human ESP deduced from its cDNA sequence obtained from odontoblasts. The human ESP has an extra peptide near its C-terminus, comprised of 25 amino acid residues, that is encoded by exons 8 and 9. These exons are derived from a tandem duplication of exon 7 in the line to humans and are not found in most mammalian species, including pig. The GAG codon in AMBN exon 7 that encodes $Gly^{154}$ is only present in some people; thus, the human ESP peptides tested in this study included variants that lacked (H-2') (SEQ ID NO: 35) or included $Gly^{154}$ (H-2) (SEQ ID NOS: 1 & 39). Based on the 40 amino acid C-terminal segment of the pig 17 kDa ESP that effectively induced cytodifferentiation of HPDL cells, the corresponding 65 amino acid residues of the human homologue were targeted for analysis.

One porcine and eleven human peptides were synthesized (Table 6) and evaluated for their bioactivity using a cell culture system consisting of HPDL cells and ST2 cells.

Figure 16:
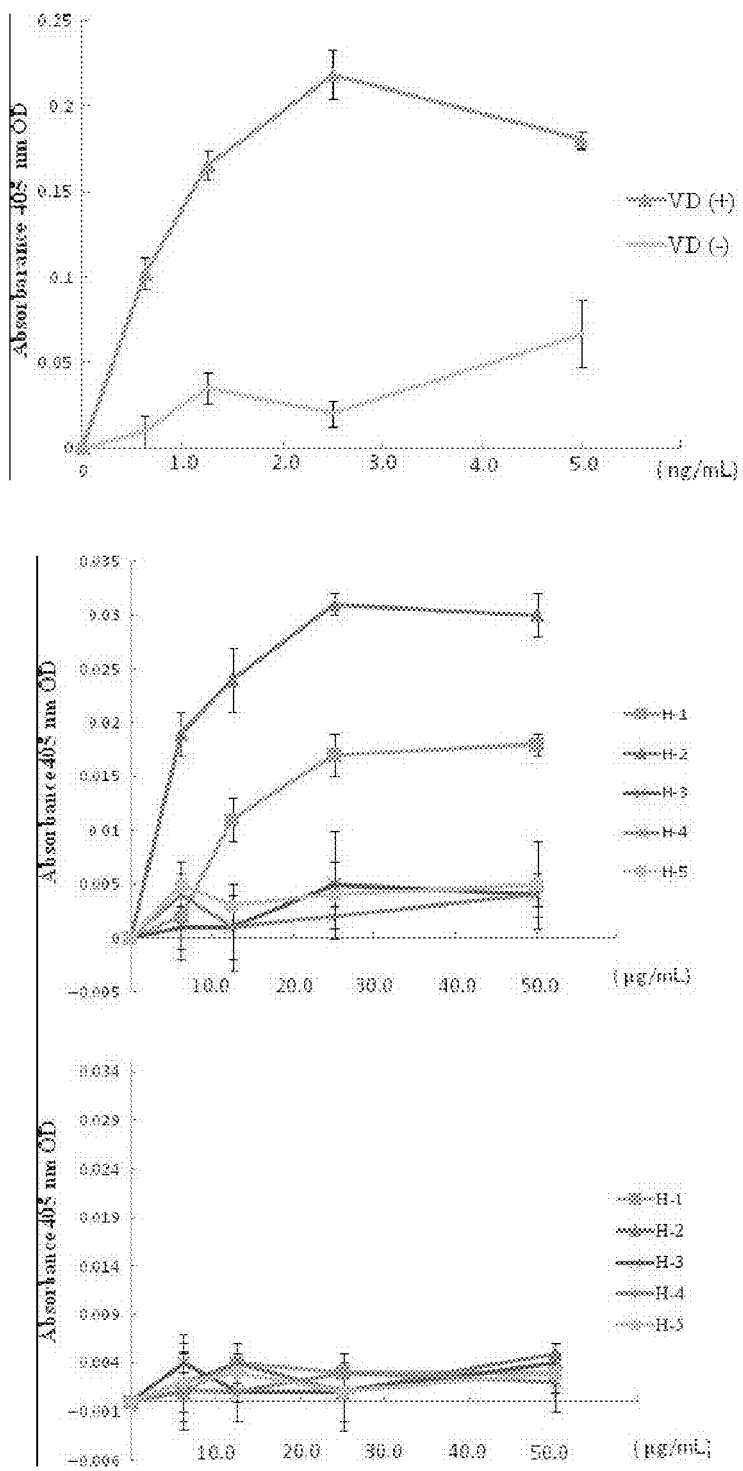
FIG. 16 shows the alkaline phosphatase (ALP) inducing activity of human synthetic peptides on human periodontal ligament fibroblast (HPDL) cells either with or without 1α-25dihydroxy-vitamin $D_3$. (A) The ALP inducing activity of HPDL cells by transforming growth factor-β1 (TGF-β1) with or without 1α-25dihydroxy-vitamin $D_3$ (VD). The ALP activity of HPDL cells was enhanced in a dose-dependent manner by TGF-β1 with 1α-25dihydroxy-vitamin $D_3$. (B) The ALP inducing activity of HPDL cells by ESP peptides (H-1 to H-5) with 1α-25dihydroxy-vitamin $D_3$. (C) The ALP inducing activity of HPDL cells by ESP peptides (H-1 to H-5) without 1α-25dihydroxy-vitamin $D_3$.
Figure 17:
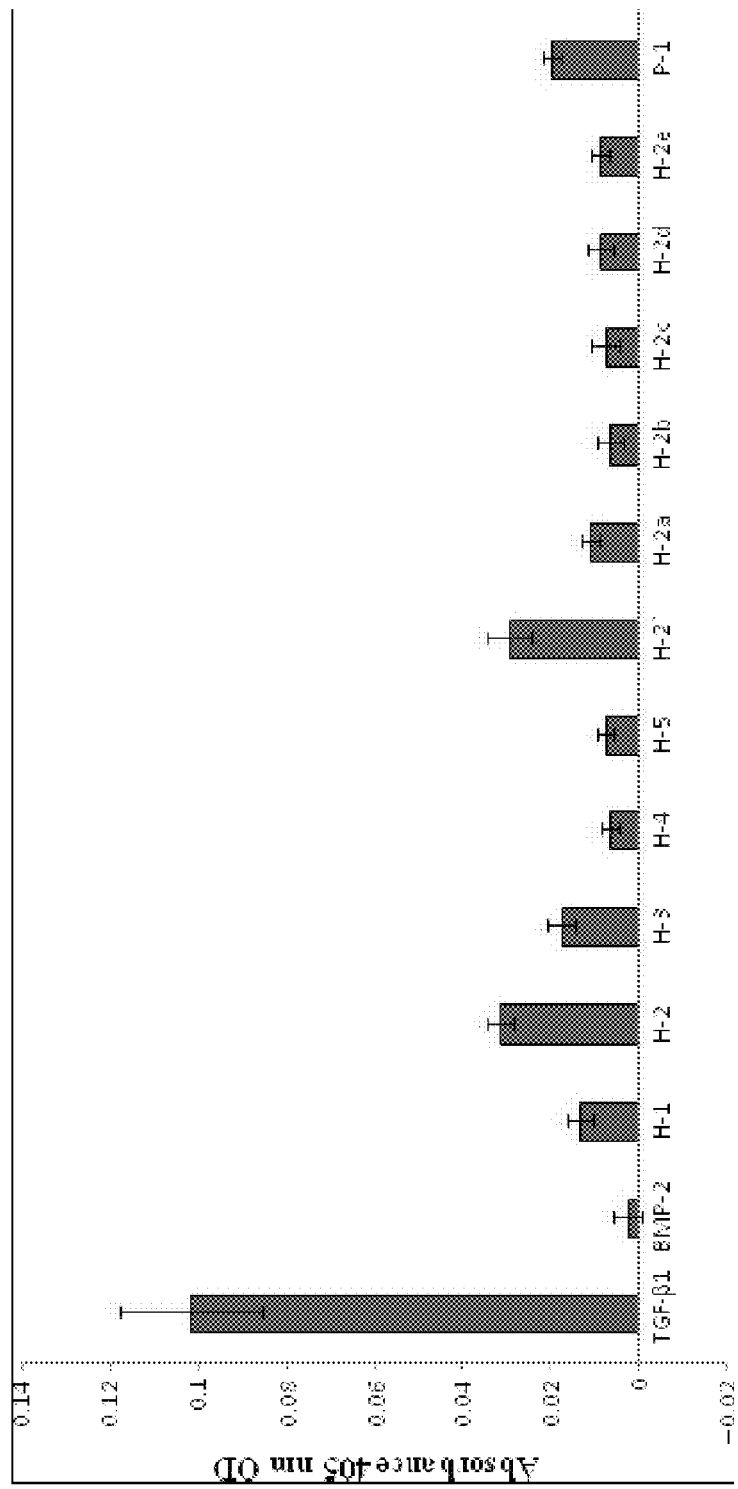
FIG. 17 shows the ALP inducing activity of HPDL cells by all synthetic ESP peptides and TGF-β1. The synthetic peptide H-2 induced higher ALP activity than the other peptides. The data represent the means±SEM of five culture wells. * Significantly different from H-2 at a value of p<0.01. All peptides were evaluated at a final concentration of 50 μg/mL in the culture system with the addition of 10 nM 1α-25dihydroxy-vitamin $D_3$. Transforming growth factor-βb1 was evaluated at a final concentration of 1 ng/mL.
Figure 18:
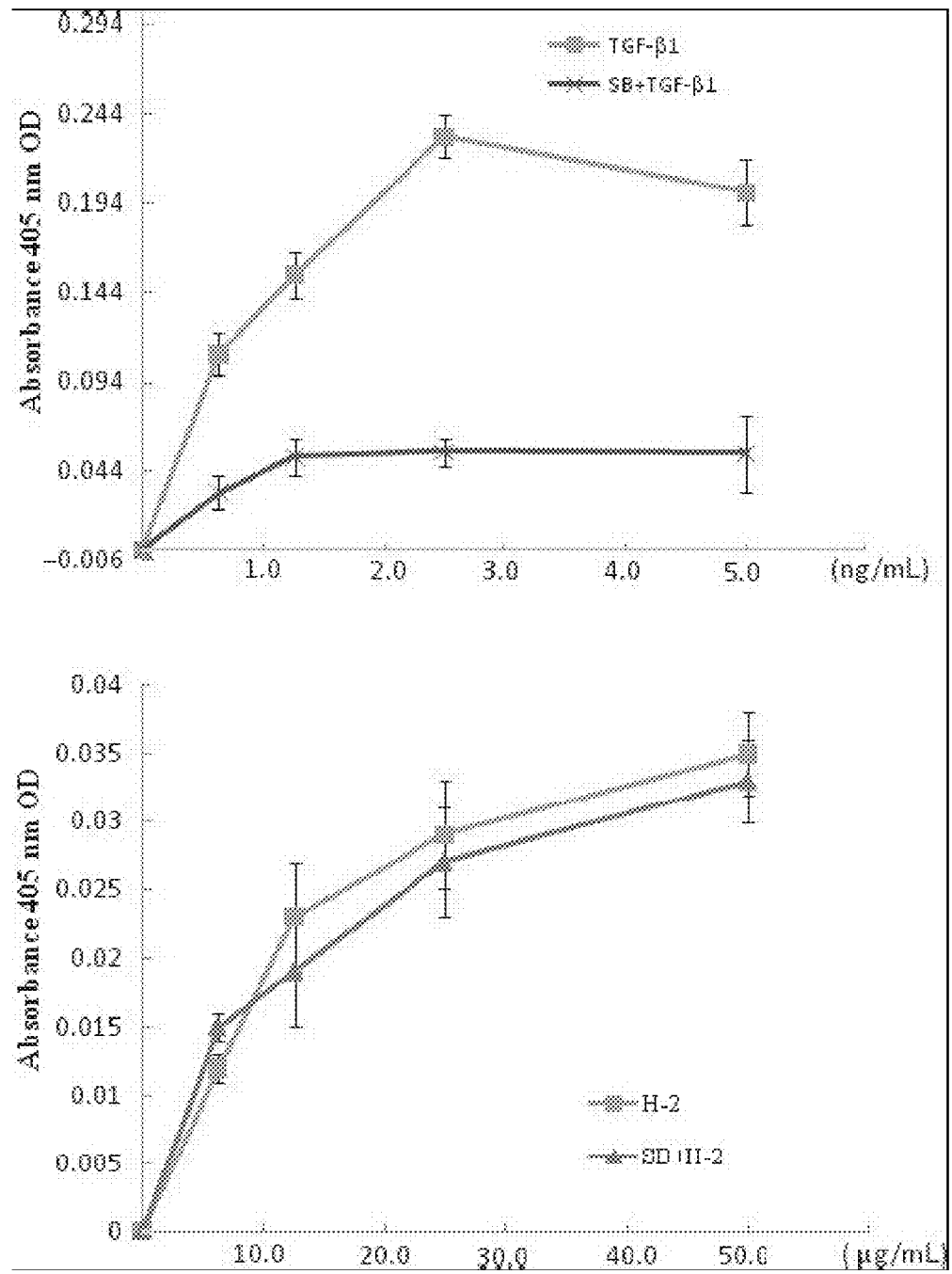
FIG. 18 shows the ALP inducing activity of human synthetic peptides and the effect of SB431542 32 (SB). The HPDL cells were cultured with the addition of 10 nM 1α-25dihydroxy-vitamin $D_3$. To investigate SB341542, 10 μM of SB431542 was added in every well. Transforming growth factor-β1 was evaluated at a final concentration range of 0-5 ng/mL.

The levels of ALP activity of HPDL cells were enhanced and stabilized by the addition of 1α-25dihydroxy-vitamin $D_3$ into the cell culture system with the application of both ESP synthetic peptides and TGF-β1 (FIG. 16). Therefore, the addition of 1α-25dihydroxy-vitamin $D_3$ to the cell culture system was employed for examination of the ALP inducing and mineralization activities of the HPDL cells. The ALP activity of HPDL cells in these conditions characteristically increased after the application of recombinant TGF-β1, but it was not influenced by BMP-2 (FIG. 17). The multiple synthetic peptides also induced ALP activity in HPDL cells, although higher concentrations were required than with TGF-β1 and none achieved ALP activity levels equal to those of TGF-β1 (FIGS. 16 and 17). The H-2 peptide had the highest ALP inducing activity of HPDL cells among the human synthetic peptides and P-1 peptide. The synthetic peptides shorter than H-2 peptide showed only a weak activity, except for the H-2' peptide (FIG. 17). These activities were not affected by the addition of SB431542, the TGF-β1 receptor inhibitor, which significantly inhibited the activity of TGF-β1 (FIG. 18). No synthetic peptide enhanced the ALP activity of ST2 cells, which was enhanced by BMP-2, but not by TGF-β1.

Figure 19:
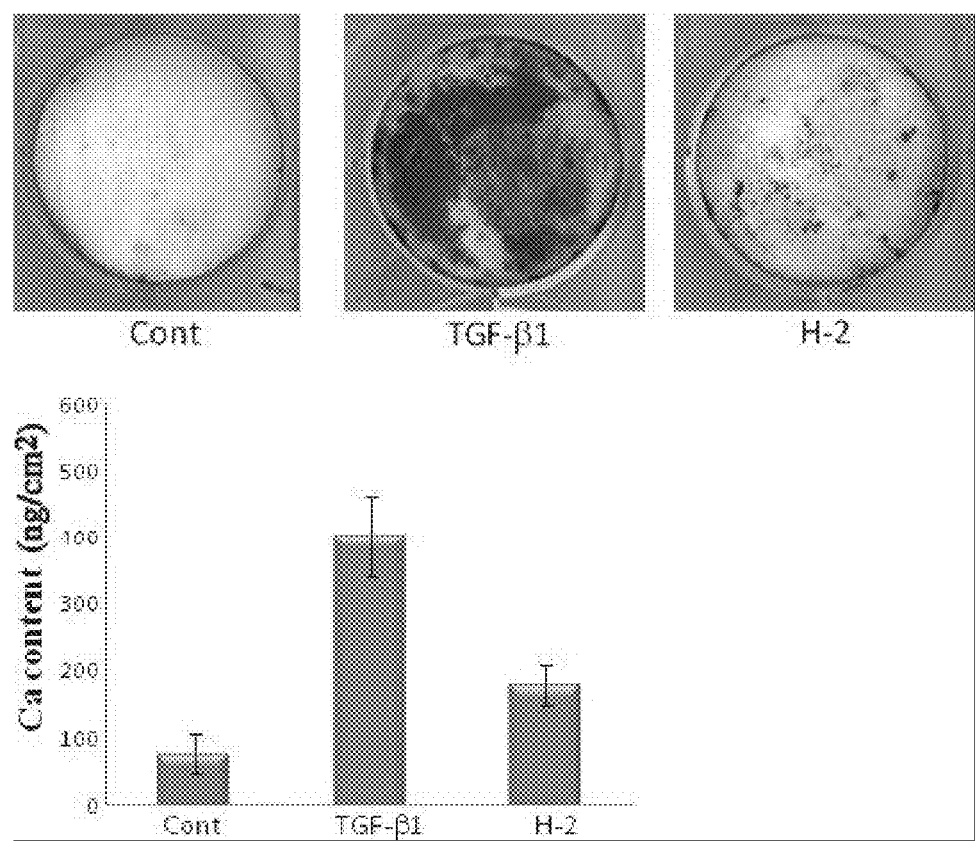
FIG. 19 shows biomineralization activity of H-2 peptide and TGF-β1. The HPDL cells were cultured for 28 d with H-2 peptide and recombinant TGF-β1 to examine the biomineralization activity and stained with Alizarin Red S (A) and measured by the calcium test (B). Transforming growth factor-β1 was evaluated at a final concentration of 1 ng/mL and H-2 peptide was at 25 μg/mL. Cont, control.

The mineralization tests of the H-2 peptide were examined using the HPDL cells in long-term cell culture because H-2 peptide demonstrated higher ALP inducing activity than the other peptides. The application of H-2 peptide induced mineralization by HPDL cells in 28 d cell culture in comparison to the control cells, in which mineralization was also detected, although its level was much lower than that of cultures containing TGF-β1 as a positive control (FIG. 19).

Figure 20:
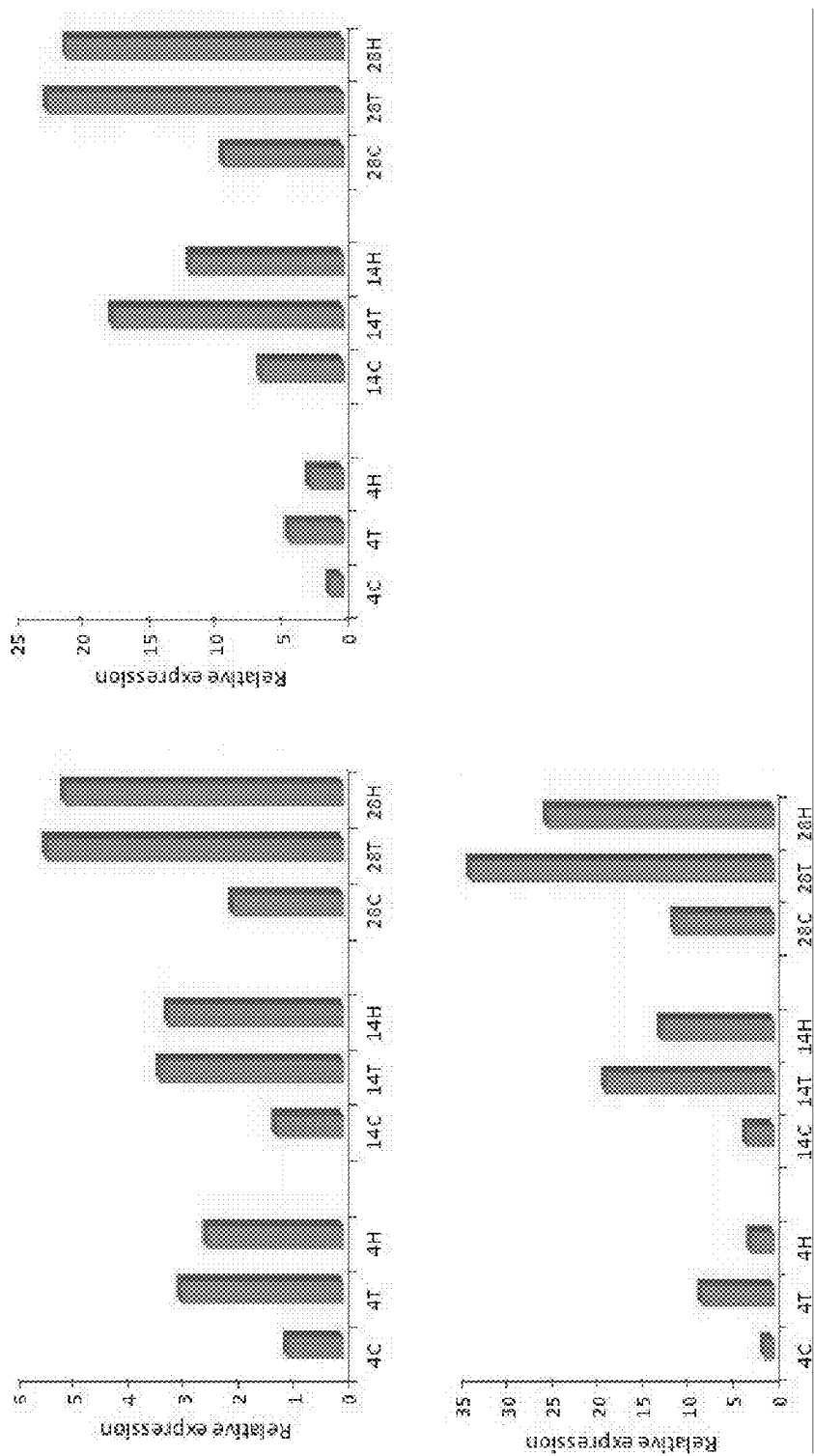
FIG. 20 shows semi-quantitative PCR with the LightCycler instrument. The expression of bone sialoprotein gene (A), osteocalcin gene (B) and osteopontin gene (C) in HPDL cells is shown in comparison with the values of 4C. Abbreviations: 4C, 4 d cultured control; 4T, cultured 4 d with TGF-β1; 4H, cultured 4 d with H-2; 14C, 14 d cultured control; 14T, cultured 14 d with TGF-β1; 14H, cultured 14 d with H-2 peptide; 28C, cultured 28 d control; 28T, cultured 28 d with TGF-β1; and 28H, cultured 28 d with H-2. Transforming growth factor-β1 was tested at a final concentration of 1 ng/mL and H-2 peptide was at 25 μg/mL.

The expressions of osteopontin, osteocalcin and bone sialoprotein, which are mineralized tissue markers related to the state of differentiation of HPDL cells, were examined in the total mRNA obtained from 4, 14 and 28 d cultured HPDL cells in the condition medium inducing the mineralization. They were expressed in all cases and increased during the culture. These expressions of the application of H-2 peptide were also closely similar to those of TGF-β1 (FIG. 20).

Multiple synthetic peptides from the human ESP increased the ALP activity and stimulated matrix mineralization in long-term cultures of HPDL cells. Semi-quantitative PCR demonstrated the osteocalcin, osteopontin and bone sialoprotein expressions to increase relative to the control values. The peptide SDKPPKPELPGVDF (SEQ ID NO: 1) had the strongest cytodifferentiation activity among all the synthetic peptides tested.

Discussion

Enamel sheath protein is produced by proteolytic cleavage, possibly by Mmp-20, from the amino-terminal side of sheathlin (ameloblastin and amelin) and is involved in the construction of the enamel sheath. Porcine ESP, with an apparent molecular mass of 17 kDa, has a stronger cementum regeneration promoting activity, which plays an important part in periodontal regeneration, than that of TGF-β1, which has been shown to have the same activity, based on the findings of an in vivo system of experimental cavities prepared in the buccal dehiscence dog model. The C-terminal region of the 17 kDa ESP appears to be the true biologically active component in this fraction, because the 15 kDa ESP, which is a cleavage product of the 17 kDa ESP lacking the C-terminal peptide, has scarcely any cementum regeneration activity at all. The 17 kDa ESP also shows a cytodifferentiation activity in a cell culture system of HPDL cells, although this activity is weaker than that of TGF-β1; however, other lower molecular weight ESPs do not demonstrate such an activity. These activities are carried by the C-terminal segment of the 17 kDa ESP; synthetic peptides of this sequence also show cytodifferentiation activity similar to the 17 kDa ESP itself in the cultured HPDL cells. Therefore, the cell culture system of HPDL cells is employed for determination of the biologically active sequence, which shows both periodontal ligament inducing activity and cytodifferentiation activity, in the C-terminal segment of the 17 kDa ESP that is missing from the smaller molecular weight ESPs.

For the purposes of periodontal ligament regeneration, peptides were synthesized corresponding to this same region of human ESP and were then evaluated to show their ALP inducing activity in the HPDL cells.

The odontoblast cell layer on the predentin of healthy human premolars was used, since enamel protein mRNAs are expressed in the porcine odontoblast cell layer. After determining the deduced amino acid sequence of the human ESP, several peptides were synthesized and evaluated for their ALP inducing activity in HPDL cells in a cell culture system. These peptides induced various amounts of HPDL cell cytodifferentiation.

The peptide SDKPPKPELPGVDF (SEQ ID NO: 1) had the most efficient cytodifferentiation activity of the human synthetic peptides and also promoted mineralization in long-term cell culture. As suspected, the peptide SDKPPK-PELPVDF (SEQ ID NO: 35), which lacks Gly[154] showed the same inductive properties. However, these sequences were different from the P-1 peptide, which carries the highest ALP inducing activity among the synthetic porcine ESP peptides tested in a previous study. There is no clear relationship between the amino acid sequences of these active synthetic peptides of human and pig ESPs.

When a TGF-β1 receptor inhibitor (SB431542) was added to the HPDL cell culture system, the ALP inducing activity of TGF-β1 was distinctly inhibited. However, the increased ALP inducing activity of HPDL cells in response to the synthetic peptide was not inhibited by adding SB431542. This suggested that the cytodifferentiation activity of the synthetic peptides is not induced via the TGF-β1 receptor. It also demonstrated that the bioactivity of the synthetic peptides was not due to TGF-β1 induced by the peptides in the HPDL cells.

The synthetic peptides had less ALP inducing activity, and higher concentrations were needed for the induction of the activity in comparison to TGF-β1. This may suggest that they are incorporated into the cells by another mechanism without the activation of a receptor, although this is currently unclear. After they are incorporated into the cells, they may be involved in the induction of ALP activity via the same cell signaling pathway as the TGF-β1, since both increase the ALP inducing activity and stimulate the mRNA of mineralized tissue markers.

In conclusion, the synthesis and evaluation of peptides corresponding to the human ESP C-terminal sequence identified the peptide sequence of the human ESP that is able to induce the cytodifferentitaon of HPDL cells in a cell culture system. Since the cytodifferentiation activity of HPDL cells may correlate with the cementum regeneration promoting activity, these results may be clinically useful for periodontal ligament regeneration.

A specific peptide sequence derived from the C-terminal side of the human ESP promotes the cytodifferentiation and mineralization activity of HPDL cells in a cell culture system.

REFERENCES

Amizuka N, Uchida T, Fukae M et al. Ultrastructural and immunocytochemical studies of enamel tufts in human permanent teeth. Arch Histol Cytol 1992; 55: 179-190.

Bartlett J, Simmer J, Xue J, Margolis H, Moreno E: Molecular cloning and mRNA tissue distribution of a novel matrix metalloproteinase isolated from porcine enamel organ. Gene 183: 123-128, 1996.

Beertsen W, VandenBos T, Everts V. Root development in mice lacking functional tissue non-specific alkaline phosphatase gene: inhibition of acellular cementum formation. J Dent Res 1999; 78: 1221-1229.

Boyan B D, Weesner T C, Lohmann C H, Andreacchio D, Carnes D L, Dean D D, Cochran D L, Schwartz Z. Porcine fetal enamel matrix derivative enhances bone formatic induced by demineralized freeze dried bone allograft in vivo. J Periodontol 2000; 71:1278-1286.

Cerny R, Slaby I, Hammarström L, Wurtz T. A novel gene expressed in rat ameloblasts codes for proteins with cell binding domains. J Bone Miner Res 1996; 11: 883-891.

Fukae M, Shimizu M: Studies on the proteins of developing bovine enamel. Arch Oral Biol 1974; 19: 381-386.

Fukae M, Tanabe T, Shimizu M: Proteolytic enzyme activity in porcine immature enamel. Tsurumi U Dent J 1977; 3: 15-17.

Fukae M, Tanabe T, Ijiri H, Shimizu M: Studies on porcine enamel proteins: a possible original enamel protein. Tsurumi U Dent J 1980; 6: 87-94.

Fukae M, Tanabe T, Shimizu M: Amino acid sequence of the main component of porcine enamel proteins. Jpn J oral Biol 1983; 25 (Suppl.) 29.

Fukae M, Tanabe T. Non-amelogenin components of porcine enamel in the protein fraction free from the enamel crystals. Calcif Tissue Int 1987a; 40:286-293.

Fukae M, Tanabe T. $^{45}$Ca-labeled proteins found in porcine developing dental enamel at an early stage of development. Adv Dent Res 1987b; 1(2): 261-266.

Fukae M, Tanabe T, Uchida T, Yamakoshi Y, Shimizu M. Enamelins in the newly formed bovine enamel. Calcif Tissue Int 1993; 53:257-261.

Fukae M, Tanabe T, Murakami C, Dohi N, Uchida T, Shimizu M. Primary structure of the porcine 89-kDa enamelin. Adv Dent Res 1996; 10: 111-118.

Fukae M, Tanabe T, Uchida T, Lee S K, Ryu O H, Murakami C, Wakida K, Simmer J P, Yamada Y, Bartlett J D: Enamelysin (matrix metalloproteinase-20): localization in the developing tooth and effects of pH and calcium on amelogenin hydrolysis. J Dent Res 77: 1580-1588, 1998.

Fukae M, Tanabe T. Degradation of enamel matrix proteins in porcine secretory enamel. Connective Tissue Res 1998; 39(1-3):123-129(427-433).

Fukae M, Kanazashi M, Nagano T, Tanabe T, Oida S, Gomi K. Porcine sheath proteins show periodontal ligament regeneration activity, Eur J Oral Sci 2006; in press.

Fukae M, Kanazashi M, Nagano T et al. Porcine sheath proteins show periodontal ligament regeneration activity. Eur J Oral Sci 2006; 114(Suppl. 1):212-218.

Fukae M, Yamamoto R, Karakida T et al. Micelle structure of amelogenin in porcine secretory enamel, 2007; 23 86:758-763.

Gestrelius S, Andersson C, Lindström D, Hammarström L, Somerman M J. In vitro studies on periodontal ligament cells and enamel matrix derivative. J Clin Periodontol 1997; 24: 685-692.

Gibson C, Yuan Z, Hall B, Longenecker G, Chen E, Thyagarajan T, Sreenath T, Wright J T, Decker S, Piddington R Harrison G, Kulkarni A. Amelogenin deficient mice display an amelogenesis imperfecta phenotype. J Biol Chem 2001; 276:31871-31875.

Hammarström L. Enamel matrix, cementum development and regeneration. J Clin Periodontol 1997; 24: 658-668.

Hammarström L, Heijl L, Gestrelius S. Periodontal regeneration in a buccal dehiscence model in monkeys after application of matrix proteins. J Clin Periodontol 1997; 24: 669-677.

Heijl L. Periodontal regeneration with matrix derivative in one human experimental defect. A case report. J Clin Periodontol 1997; 24: 693-696.

Heijl L, Heden G, Svärdström G, Östgren A. Enamel matrix derivative (EMDOGAIN®) in the treatment of intrabony periodontal defects. J Clin Periodontol 1997; 24: 705-714.

Hsu S M, Aine L R, Fanger H. A comparative study of the perioxidase-antiperioxidase method and an avidin-biotin complex method for studying the polypeptide hormones with radioimmunoassay antibodies. Am J Clin Pathol 1981; 75:734-738.

Hu C C, Bartlett J D, Zhang C H, Ryu O H, Simmer J p: Cloning cDNA sequence, and alternative splicing of porcine amelogenin mRNAs. *J Dent Res* 1996; 75: 1735-1741.

Hu C-C, Fukae M, Uchida T, Qian Q, Zhang C H, Ryu O H, Tanabe T, Yamakoshi Y, Murakami C, Dohi N, Shimizu M, Simmer J P. Sheathlin: cloning, cDNA/polypeptide sequences, and immunolocalization of porcine enamel sheath proteins. *J Dent Res* 1997a; 76: 648-657.

Hu C-C, Fukae M, Uchida T, Qian Q, Zhang C H, Ryu O H, Tanabe T, Yamakoshi Y, Murakami C, Dohi N, Shimizu M, Simmer J P. Cloning and characterization of porcine enamelin mRNAs. *J Dent Res* 1997b; 76: 1720-1729.

Hu C-C, Hu Y, Smith C S. Enamel defects and ameloblast-specific expression in Enam knock-out/lacZ knock-in mice. J Biol Chem 2008; 18:10858-10871.

Ikawa T, Kakegawa A, Nagano T, Ando H, Yamakoshi Y, Tanabe T, Simmer J P, Hu C C, Fuake M, Oida S. Porcine amelogenin is expressed from the X and Y chromosomes. *J Dent Res* 2005; 84: 144-148.

Iwata T, Morotome M, Tanabe T, Fukae M, Ishikawa I, Oida S, Noggin blocks osteoinductive activity of porcine enamel extracts. *J Dent Res* 2002; 81: 387-391.

Iwata T, Yamakoshi Y, Hu J C et al. Processing of ameloblastin by MMP-20. J Dent Res 2007; 86:153-157.

Kakegawa A, Oida S, Gomi K, Nagano T, Yamakoshi Y, Fukui T, Kanazashi M, Arai T, Fukae M., Cytodifferentiation activity of synthetic human enamel sheath protein peptides, J Periodont Res 2010 [in press].

Kanazashi M, Gomi K, Tanabe T, Nagano T, Fukae M, Arai T. Periodontal regeneration activity of protein fractions obtained from the enamel matrix derivatives by the ammonium sulfate fractionation (Japanese). *Tsurumi Univ Dent J* 2004; 30: 225-230.

Kanazashi M, Gomi K, Nagano T, Tanabe T, Arai T, Fukae M. The 17-kDa sheath protein in enamel proteins induces cementum regeneration in experimental cavities created in a buccal dehiscence model of dogs. *J periodont Res* 2006; 41:193-199

Kawase T, Okuda K, Momose M, Kato Y, Yoshie H, Burns D M. Enamel matrix derivative (EMDOGAIN®) rapidly stimulates phosphorylation of the MAP kinase family and nuclear accumulation of smad2 in both oral epithelial and fibroblastic human cells. *J Periodontal Res* 2001; 36:367-376.

Krebsbach P H, Lee S K, Matsuki Y, Kozak C A, Yamada K M, Yamada Y. Full-length sequence, localization, and chromosomal mapping of ameloblastin: a novel tooth-specific gene. *J Biol Chem* 1996; 271: 4431-4435.

Laemmli U K. Cleavage of structural proteins during the assembly of the head of bacteriophage T4. *Nature* 1970; 227: 680-688.

Murakami C, Dohi N, Fukae M, Tanabe T, Yamakoshi Y, Wakida K, Satoda T, Takahashi O, Shimizu M, Ryu O H, Simmer J P, Uchida T. Immunochemical and immunohistochemical study of 27 and 29 kDa calcium binding proteins and related proteins in the porcine tooth germ. *Histochem Cell Biol* 1997; 107: 485-494.

Nagano T. Effects of fractionated porcine enamel proteins on osteogenesis in human periodontal ligament (HPDL) cells in vitro (Japanese). *J Jpn Soc Periodontol* 2003; 45: 384-393.

Nagano T, Oida S, Ando H, Gomi K, Arai T, Fukae M. Relative levels of mRNA encoding enamel proteins in enamel organ epithelia and odontoblasts. J Dent Res 2003; 82:982-986.

Nagano T, Iwata T, Ogata Y, Tanabe T, Gomi K, Fukae M, Arai T, Oida S. Effect of heat treatment on bioactivities of enamel matrix derivatives in human periodontal ligament (HPDL) cells. J periodont Res 2004; 39:249-256.

Oida s, Nagano T, Yamakoshi Y, Ando H, Yamada M, Fukae M. Amelogenin gene expression in porcine odontoblasts. J Den Res 2002; 81: 103-108.

Shimizu M, Tanabe T, Fukae M: Proteolytic enzyme in porcine immature enamel. J Dent Res 58B: 782-788, 1979.

Shimizu M, Fukae M: Enamel proteins. In Mechnisms of Tooth Enamel Formation (ed. by S. Suga): 125-141, Quitessence Publishing Co. Inc., Tokyo, 1983.

Shimokawa H, Ogata Y, Sasaki S, Sobel M E, McQuillan C I, Termine J D, Young M F. Molecular cloning of bovine amelogenin cDNA. *Adv Dent Res* 1987; 1: 293-297.

Simmer J P, Fukae M, Tanabe T, Yamakoshi Y, Uchida T, Xue J, Margolis H C, Shimizu M, DeHart B C, Hu C C, Bartlett J D. Purification, characterization, and cloning of enamel matrix serine proteinase 1. *J Dent Res* 1998; 77: 377-386.

Snead M L, Lau E C, Zeichner-David M, Fincham A G, Woo S L C, Slavkin H C. DNA sequence for cloned cDNA for murine amelogenin reveals the amino acid sequence for enamel specific protein. *Biochem Biophys Res Commun* 1985; 129:812-818.

Somerman M J, Archer S Y, Imm G R, Foster R A. A comparative study of human periodontal ligament cells and gingival fibroblasts in vitro. *J Dent Res* 1988; 67: 66-70.

Suzuki S, Nagano T, Yamakoshi Y, Gomi K, Arai T, Fukae M, KatagiriT, Oida S. Enamel matrix derivative gel stimulates signal transduction of BMP and TGF-. *J Dent Res* 2005; 84:510-514.

Tanabe T. Purification and characterization of proteolytic enzyme in porcine immature enamel (Japanese). *Tsurumi Univ Dent J* 1984; 10: 443-452.

Tanabe T, Aoba T, Moreno E C, Fukae M, Shimizu M. properties of phosphorylated 32 kd nonamelogenin proteins isolated from porcine secretory enamel. *Calcif Tissue Int* 1990; 46:205-215.

Tanabe T, Fukae M, Uchida T, Shimizu M. The localization and characterization of proteinases for the initial cleavage of porcine amelogenin. *Calcif Tissue Int* 1992; 51: 213-217.

Tanabe T, Fukae M, Shimizu M: Possible actions of metalloproteinases found in porcine enamel in an early secretory stage. Adv Dent Res 10(2): 170-172, 1996.

Toyosawa S, Fujisawa T, Ooshima T et al. Cloning and characterization of the human ameloblastin gene. Gene 2000; 256: 1-11.

Uchida T, Tanabe T, Fukae M, Shimizu M, Yamada M, Miake K, Kobayashi S. Immunochemical and immunohistochemical studies, using antisera against 25 kDa amelogenin, 89 kDa enamelin and the 13-17 kDa nonamelogenins, on immature enamel of the pig and rat. *Histochemistry* 1991; 96: 129-138.

Uchida T, Fukae M, Tanabe T, Yamakoshi S, Satoda T, Murakami C, Takahashi O, Shimizu M. Immunochemical and immunocytochemical study of a 15 kDa non-amelogenin and related proteins in the porcine immature enamel: proposal of a new group of enamel proteins 'Sheath Proteins'. *Biomedical Research* 1995; 16: 131-140.

Yamakoshi Y, Tanabe T, Fukae M, Shimizu M. Porcine amelogenins. *Calcif Tissue Int* 1994; 54: 69-75.

Yamakoshi Y, Tanabe T, Oida S, Hu C-C, Simmer J P, Fukae M. Calcium binding of enamel proteins and their derivatives with emphasis on the calcium-binding domain of porcine sheathlin. *Archives of Oral Biology* 2001; 46:1005-1014.

Zetterström O, Andersson C, Eriksson L, Fredriksson A, Friskopp J, Heden G, Jansson B, Lundgren T, Nilveus R, Olsson A, Renvert S, Salonen L, Sjöström L, Winell A, Östgren A, Gestrelius S: Clinical safety of enamel matrix derivative (EMDOGAIN®) in the treatment of periodontal defects. *J Clin Periodontol* 1997; 24: 697-704.

The invention claimed is:

1. A composition comprising an isolated polypeptide comprising SEQ ID NO: 36.

2. A method of treatment for periodontal disease, comprising administering a pharmaceutically effective amount of the composition of claim 1 to a human or mammal in need thereof.

3. The method of claim 2, wherein the periodontal disease is periodontitis.

4. The method of claim 2, wherein the treatment comprises periodontal tissue regeneration.

5. The method of claim 2, wherein the treatment comprises cementum regeneration.

6. The method of claim 2, wherein the treatment comprises cytodifferentiation of periodontal ligament cells.

7. A composition comprising an isolated polypeptide selected from the group consisting of an isolated polypeptide consisting of SEQ ID NO: 35 and an isolated polypeptide consisting SEQ ID NO: 36.

8. A method of treatment for periodontal disease, comprising administering a pharmaceutically effective amount of the composition of claim 7 to a human or mammal in need thereof.

9. The method of claim 8, wherein the periodontal disease is periodontitis.

10. The method of claim 8, wherein the treatment comprises periodontal tissue regeneration.

11. The method of claim 8, wherein the treatment comprises cementum regeneration.

12. The method of claim 8, wherein the treatment comprises cytodifferentiation of periodontal ligament cells.

13. A composition comprising an isolated polypeptide consisting of the polypeptide sequence of SEQ ID NO: 36, wherein the polypeptide sequence comprises amino acid residues 144-156 which corresponds to amino acid residues 1-13 of SEQ ID NO: 35.

14. A method of treatment for periodontal disease, comprising administering a pharmaceutically effective amount of the composition of claim 13 to a human or mammal in need thereof.

15. The method of claim 14, wherein the periodontal disease is periodontitis.

16. The method of claim 14, wherein the treatment comprises periodontal tissue regeneration.

17. The method of claim 14, wherein the treatment comprises cementum regeneration.

18. The method of claim 14, wherein the treatment comprises cytodifferentiation of periodontal ligament cells.

* * * * *

SEQUENCE LISTING

<160> NUMBER OF SEQ ID NOS: 50

<210> SEQ ID NO 1
<211> LENGTH: 14
<212> TYPE: PRT
<213> ORGANISM: Homo sapiens
<220> FEATURE:
<223> OTHER INFORMATION: 14 aa from 144 to 157 in sequence 11

<400> SEQUENCE: 1

Ser Asp Lys Pro Pro Lys Pro Glu Leu Pro Gly Val Asp Phe
1               5                   10

<210> SEQ ID NO 2
<211> LENGTH: 14
<212> TYPE: PRT
<213> ORGANISM: Homo sapiens
<220> FEATURE:
<223> OTHER INFORMATION: 14 aa from 157 to 170 in sequence 11

<400> SEQUENCE: 2

Phe Ala Asp Pro Gln Gly Pro Ser Leu Pro Gly Met Asp Phe
1               5                   10

<210> SEQ ID NO 3
<211> LENGTH: 14
<212> TYPE: PRT
<213> ORGANISM: Homo sapiens
<220> FEATURE:
<223> OTHER INFORMATION: 14 aa from 131 to 144 in sequence 11

<400> SEQUENCE: 3

Glu Gly Glu Leu Pro Leu Val Gln Gln Val Ala Pro Ser
1               5                   10

<210> SEQ ID NO 4
<211> LENGTH: 14
<212> TYPE: PRT
<213> ORGANISM: Homo sapiens
<220> FEATURE:
<223> OTHER INFORMATION: 14 aa from 170 to 183 in sequence 11

<400> SEQUENCE: 4

Phe Pro Asp Pro Gln Gly Pro Ser Leu Pro Gly Leu Asp Phe
1               5                   10

<210> SEQ ID NO 5
<211> LENGTH: 14
<212> TYPE: PRT
<213> ORGANISM: Homo sapiens
<220> FEATURE:
<223> OTHER INFORMATION: 14 aa from 183 to 196 in sequence 11

<400> SEQUENCE: 5

Phe Ala Asp Pro Gln Gly Ser Thr Ile Phe Gln Ile Ala Arg
1               5                   10

<210> SEQ ID NO 6
<211> LENGTH: 6
<212> TYPE: PRT
<213> ORGANISM: Homo sapiens
<220> FEATURE:
<223> OTHER INFORMATION: 6 aa from 1 to 6 in sequence 9, 14, 33 and 34

<400> SEQUENCE: 6

Met Pro Leu Pro Pro His

-continued

<210> SEQ ID NO 7
<211> LENGTH: 6
<212> TYPE: PRT
<213> ORGANISM: Homo sapiens
<220> FEATURE:
<223> OTHER INFORMATION: 6 aa from 7 to 12 in sequence 9, 14, 33 and 34

<400> SEQUENCE: 7

Pro Gly His Pro Gly Tyr
1               5

<210> SEQ ID NO 8
<211> LENGTH: 6
<212> TYPE: PRT
<213> ORGANISM: Homo sapiens
<220> FEATURE:
<223> OTHER INFORMATION: 6 aa from 12 to 17 in sequence 9, 14, 33 and 34

<400> SEQUENCE: 8

Tyr Ile Asn Phe Ser Tyr
1               5

<210> SEQ ID NO 9
<211> LENGTH: 17
<212> TYPE: PRT
<213> ORGANISM: Homo sapiens
<220> FEATURE:
<223> OTHER INFORMATION: 17 aa from 1 to 17 in sequence 14, 33 and 34

<400> SEQUENCE: 9

Met Pro Leu Pro Pro His Pro Gly His Pro Gly Tyr Ile Asn Phe Ser
1               5                   10                  15

Tyr

<210> SEQ ID NO 10
<211> LENGTH: 170
<212> TYPE: PRT
<213> ORGANISM: Sus scrofa
<220> FEATURE:
<223> OTHER INFORMATION: porcine sheath protein

<400> SEQUENCE: 10

Val Pro Ala Phe Pro Arg Gln Pro Gly Thr Pro Gly Val Ala Ser Leu
1               5                   10                  15

Ser Leu Glu Thr Met Arg Gln Leu Gly Ser Leu Gln Gly Leu Asn Met
            20                  25                  30

Leu Ser Gln Tyr Ser Arg Phe Gly Phe Gly Lys Ser Phe Asn Ser Leu
        35                  40                  45

Trp Met His Gly Leu Leu Pro Pro His Ser Ser Phe Gln Trp Met Arg
    50                  55                  60

Pro Arg Glu His Glu Thr Gln Gln Tyr Gly Tyr Ser Leu Pro Val His
65                  70                  75                  80

Pro Pro Pro Leu Pro Ser Gln Pro Ser Leu Gln Pro Gln Gln Pro Gly
                85                  90                  95

Gln Lys Pro Phe Leu Gln Pro Thr Val Val Thr Ser Ile Gln Asn Pro
            100                 105                 110

Val Gln Lys Gly Val Pro Gln Pro Pro Ile Tyr Gln Gly His Pro Pro
        115                 120                 125

Leu Gln Gln Val Glu Gly Pro Met Val Gln Gln Val Ala Pro Ser
    130                 135                 140

```
Glu Lys Pro Pro Glu Ala Glu Leu Pro Gly Leu Asp Phe Ala Asp Pro
145                 150                 155                 160

Gln Asp Pro Ser Met Phe Pro Ile Ala Arg
                165                 170

<210> SEQ ID NO 11
<211> LENGTH: 196
<212> TYPE: PRT
<213> ORGANISM: Homo sapiens
<220> FEATURE:
<223> OTHER INFORMATION: human sheath protein

<400> SEQUENCE: 11

Val Pro Phe Phe Pro Gln Gln Ser Gly Thr Pro Gly Met Ala Ser Leu
1               5                   10                  15

Ser Leu Glu Thr Met Arg Gln Leu Gly Ser Leu Gln Arg Leu Asn Thr
            20                  25                  30

Leu Ser Gln Tyr Ser Arg Tyr Gly Phe Gly Lys Ser Phe Asn Ser Leu
        35                  40                  45

Trp Met His Gly Leu Leu Pro Pro His Ser Ser Leu Pro Trp Met Arg
    50                  55                  60

Pro Arg Glu His Glu Thr Gln Gln Tyr Glu Tyr Ser Leu Pro Val His
65                  70                  75                  80

Pro Pro Pro Leu Pro Ser Gln Pro Ser Leu Lys Pro Gln Gln Pro Gly
                85                  90                  95

Gln Lys Pro Phe Leu Gln Ser Ala Ala Ala Thr Thr Asn Gln Ala Thr
            100                 105                 110

Ala Leu Lys Glu Ala Leu Gln Pro Pro Ile His Leu Gly His Leu Pro
        115                 120                 125

Leu Gln Glu Gly Glu Leu Pro Leu Val Gln Gln Val Ala Pro Ser
    130                 135                 140

Asp Lys Pro Pro Lys Pro Glu Leu Pro Gly Val Asp Phe Ala Asp Pro
145                 150                 155                 160

Gln Gly Pro Ser Leu Pro Gly Met Asp Phe Pro Asp Pro Gln Gly Pro
                165                 170                 175

Ser Leu Pro Gly Leu Asp Phe Ala Asp Pro Gln Gly Ser Thr Ile Phe
            180                 185                 190

Gln Ile Ala Arg
        195

<210> SEQ ID NO 12
<211> LENGTH: 40
<212> TYPE: PRT
<213> ORGANISM: Sus scrofa
<220> FEATURE:
<223> OTHER INFORMATION: 40 aa from 131 to 170 in sequence 10

<400> SEQUENCE: 12

Gln Val Glu Gly Pro Met Val Gln Gln Val Ala Pro Ser Glu Lys
1               5                   10                  15

Pro Pro Glu Ala Glu Leu Pro Gly Leu Asp Phe Ala Asp Pro Gln Asp
            20                  25                  30

Pro Ser Met Phe Pro Ile Ala Arg
        35                  40

<210> SEQ ID NO 13
<211> LENGTH: 66
<212> TYPE: PRT
<213> ORGANISM: Homo sapiens
<220> FEATURE:
```

-continued

<223> OTHER INFORMATION: 66 aa from 131 to 196 in sequence 11

<400> SEQUENCE: 13

Glu Gly Glu Leu Pro Leu Val Gln Gln Gln Val Ala Pro Ser Asp Lys
1               5                   10                  15

Pro Pro Lys Pro Glu Leu Pro Gly Val Asp Phe Ala Asp Pro Gln Gly
            20                  25                  30

Pro Ser Leu Pro Gly Met Asp Phe Pro Asp Pro Gln Gly Pro Ser Leu
        35                  40                  45

Pro Gly Leu Asp Phe Ala Asp Pro Gln Gly Ser Thr Ile Phe Gln Ile
    50                  55                  60

Ala Arg
65

<210> SEQ ID NO 14
<211> LENGTH: 45
<212> TYPE: PRT
<213> ORGANISM: Sus scrofa
<220> FEATURE:
<223> OTHER INFORMATION: porcine 6 kDa amelogenin

<400> SEQUENCE: 14

Met Pro Leu Pro Pro His Pro Gly His Pro Gly Tyr Ile Asn Phe Ser
1               5                   10                  15

Tyr Glu Val Leu Thr Pro Leu Lys Trp Tyr Gln Asn Met Ile Arg His
            20                  25                  30

Pro Tyr Thr Ser Tyr Gly Tyr Glu Pro Met Gly Gly Trp
        35                  40                  45

<210> SEQ ID NO 15
<211> LENGTH: 15
<212> TYPE: PRT
<213> ORGANISM: Homo sapiens
<220> FEATURE:
<223> OTHER INFORMATION: 15 aa from 1 to 15 in sequence 14, 33 and 34

<400> SEQUENCE: 15

Met Pro Leu Pro Pro His Pro Gly His Pro Gly Tyr Ile Asn Phe
1               5                   10                  15

<210> SEQ ID NO 16
<211> LENGTH: 16
<212> TYPE: PRT
<213> ORGANISM: Sus scrofa
<220> FEATURE:
<223> OTHER INFORMATION: 16 aa from 15 to 30 in sequence 14

<400> SEQUENCE: 16

Phe Ser Tyr Glu Val Leu Thr Pro Leu Lys Trp Tyr Gln Asn Met Ile
1               5                   10                  15

<210> SEQ ID NO 17
<211> LENGTH: 16
<212> TYPE: PRT
<213> ORGANISM: Sus scrofa
<220> FEATURE:
<223> OTHER INFORMATION: 16 aa from 30 to 45 in sequence 14

<400> SEQUENCE: 17

Ile Arg His Pro Tyr Thr Ser Tyr Gly Tyr Glu Pro Met Gly Gly Trp
1               5                   10                  15

<210> SEQ ID NO 18
<211> LENGTH: 13

```
<212> TYPE: PRT
<213> ORGANISM: Sus scrofa
<220> FEATURE:
<223> OTHER INFORMATION: 13 aa from 1 to 13 in sequence 10 and 24

<400> SEQUENCE: 18

Val Pro Ala Phe Pro Arg Gln Pro Gly Thr Pro Gly Val
1               5                   10

<210> SEQ ID NO 19
<211> LENGTH: 13
<212> TYPE: PRT
<213> ORGANISM: Sus scrofa
<220> FEATURE:
<223> OTHER INFORMATION: 13 aa from 9 to 22 in sequence 10 and 24

<400> SEQUENCE: 19

Thr Pro Gly Val Ala Ser Leu Ser Leu Glu Thr Met Arg
1               5                   10

<210> SEQ ID NO 20
<211> LENGTH: 13
<212> TYPE: PRT
<213> ORGANISM: Sus scrofa
<220> FEATURE:
<223> OTHER INFORMATION: 13 aa from 19 to 31 in sequence 10 and 24

<400> SEQUENCE: 20

Glu Thr Met Arg Gln Leu Gly Ser Leu Gln Gly Leu Asn
1               5                   10

<210> SEQ ID NO 21
<211> LENGTH: 15
<212> TYPE: PRT
<213> ORGANISM: Sus scrofa
<220> FEATURE:
<223> OTHER INFORMATION: 15 aa from 132 to 146 in sequence 10

<400> SEQUENCE: 21

Val Glu Gly Pro Met Val Gln Gln Val Ala Pro Ser Glu Lys
1               5                   10                  15

<210> SEQ ID NO 22
<211> LENGTH: 15
<212> TYPE: PRT
<213> ORGANISM: Sus scrofa
<220> FEATURE:
<223> OTHER INFORMATION: 15 aa from 144 to 158 in sequence 10

<400> SEQUENCE: 22

Ser Glu Lys Pro Pro Glu Ala Glu Leu Pro Gly Leu Asp Phe Ala
1               5                   10                  15

<210> SEQ ID NO 23
<211> LENGTH: 15
<212> TYPE: PRT
<213> ORGANISM: Sus scrofa
<220> FEATURE:
<223> OTHER INFORMATION: 15 aa from 156 to 170 in sequence 10

<400> SEQUENCE: 23

Asp Phe Ala Asp Pro Gln Asp Pro Ser Met Phe Pro Ile Ala Arg
1               5                   10                  15

<210> SEQ ID NO 24
<211> LENGTH: 31
<212> TYPE: PRT
<213> ORGANISM: Sus scrofa
```

```
<220> FEATURE:
<223> OTHER INFORMATION: 31 aa from 1 to 31 in sequence 10

<400> SEQUENCE: 24

Val Pro Ala Phe Pro Arg Gln Pro Gly Thr Pro Gly Val Ala Ser Leu
1               5                   10                  15

Ser Leu Glu Thr Met Arg Gln Leu Gly Ser Leu Gln Gly Leu Asn
            20                  25                  30

<210> SEQ ID NO 25
<211> LENGTH: 31
<212> TYPE: PRT
<213> ORGANISM: Homo sapiens
<220> FEATURE:
<223> OTHER INFORMATION: 31 aa from 1 to 31 in sequence 11

<400> SEQUENCE: 25

Val Pro Phe Phe Pro Gln Gln Ser Gly Thr Pro Gly Met Ala Ser Leu
1               5                   10                  15

Ser Leu Glu Thr Met Arg Gln Leu Gly Ser Leu Gln Arg Leu Asn
            20                  25                  30

<210> SEQ ID NO 26
<211> LENGTH: 8
<212> TYPE: PRT
<213> ORGANISM: Homo sapiens
<220> FEATURE:
<223> OTHER INFORMATION: 8 aa from 150 to 157 in sequence 11

<400> SEQUENCE: 26

Pro Glu Leu Pro Gly Val Asp Phe
1               5

<210> SEQ ID NO 27
<211> LENGTH: 8
<212> TYPE: PRT
<213> ORGANISM: Homo sapiens
<220> FEATURE:
<223> OTHER INFORMATION: 8 aa from 163 to 170 in sequence 11

<400> SEQUENCE: 27

Pro Ser Leu Pro Gly Met Asp Phe
1               5

<210> SEQ ID NO 28
<211> LENGTH: 6
<212> TYPE: PRT
<213> ORGANISM: Homo sapiens
<220> FEATURE:
<223> OTHER INFORMATION: 6 aa from 152 to 157 in sequence 11

<400> SEQUENCE: 28

Leu Pro Gly Val Asp Phe
1               5

<210> SEQ ID NO 29
<211> LENGTH: 6
<212> TYPE: PRT
<213> ORGANISM: Homo sapiens
<220> FEATURE:
<223> OTHER INFORMATION: 6 aa from 165 to 170 in sequence 11

<400> SEQUENCE: 29

Leu Pro Gly Met Asp Phe
1               5
```

-continued

```
<210> SEQ ID NO 30
<211> LENGTH: 5
<212> TYPE: PRT
<213> ORGANISM: Homo sapiens
<220> FEATURE:
<223> OTHER INFORMATION: 5 aa from 150 to 154 in sequence 11

<400> SEQUENCE: 30

Pro Glu Leu Pro Gly
1               5

<210> SEQ ID NO 31
<211> LENGTH: 5
<212> TYPE: PRT
<213> ORGANISM: Sus scrofa
<220> FEATURE:
<223> OTHER INFORMATION: 5 aa from 163 to 167 in sequence 10

<400> SEQUENCE: 31

Pro Ser Leu Pro Gly
1               5

<210> SEQ ID NO 32
<211> LENGTH: 3
<212> TYPE: PRT
<213> ORGANISM: Homo sapiens
<220> FEATURE:
<223> OTHER INFORMATION: 3 aa from 152 to 154 or from 165 to 167 in
      sequence 11

<400> SEQUENCE: 32

Leu Pro Gly
1

<210> SEQ ID NO 33
<211> LENGTH: 45
<212> TYPE: PRT
<213> ORGANISM: Homo sapiens
<220> FEATURE:
<223> OTHER INFORMATION: human 6 kDa amelogenin derived from Y-linked

<400> SEQUENCE: 33

Met Pro Leu Pro Pro His Pro Gly His Pro Gly Tyr Ile Asn Phe Ser
1               5                   10                  15

Tyr Glu Val Leu Thr Pro Leu Lys Trp Tyr Gln Ser Met Ile Arg Pro
            20                  25                  30

Pro Tyr Ser Ser Tyr Gly Tyr Glu Pro Met Gly Gly Trp
        35                  40                  45

<210> SEQ ID NO 34
<211> LENGTH: 44
<212> TYPE: PRT
<213> ORGANISM: Homo sapiens
<220> FEATURE:
<223> OTHER INFORMATION: human 6 kDa amelogenin derived from X-linked

<400> SEQUENCE: 34

Met Pro Leu Pro Pro His Pro Gly His Pro Gly Tyr Ile Asn Phe Ser
1               5                   10                  15

Tyr Glu Val Leu Thr Pro Leu Lys Trp Tyr Gln Ser Ile Arg Pro Pro
            20                  25                  30

Tyr Pro Ser Tyr Gly Tyr Glu Pro Met Gly Gly Trp
        35                  40

<210> SEQ ID NO 35
<211> LENGTH: 13
```

```
<212> TYPE: PRT
<213> ORGANISM: Homo sapiens
<220> FEATURE:
<223> OTHER INFORMATION: 13 aa from 144 to 156 in sequence 36

<400> SEQUENCE: 35

Ser Asp Lys Pro Pro Lys Pro Glu Leu Pro Val Asp Phe
1               5                   10

<210> SEQ ID NO 36
<211> LENGTH: 195
<212> TYPE: PRT
<213> ORGANISM: Homo sapiens
<220> FEATURE:
<223> OTHER INFORMATION: 195 aa from human sheath protein

<400> SEQUENCE: 36

Val Pro Phe Phe Pro Gln Gln Ser Gly Thr Pro Gly Met Ala Ser Leu
1               5                   10                  15

Ser Leu Glu Thr Met Arg Gln Leu Gly Ser Leu Gln Arg Leu Asn Thr
            20                  25                  30

Leu Ser Gln Tyr Ser Arg Tyr Gly Phe Gly Lys Ser Phe Asn Ser Leu
        35                  40                  45

Trp Met His Gly Leu Leu Pro Pro His Ser Ser Leu Pro Trp Met Arg
    50                  55                  60

Pro Arg Glu His Glu Thr Gln Gln Tyr Glu Tyr Ser Leu Pro Val His
65                  70                  75                  80

Pro Pro Pro Leu Pro Ser Gln Pro Ser Leu Lys Pro Gln Gln Pro Gly
                85                  90                  95

Gln Lys Pro Phe Leu Gln Ser Ala Ala Ala Thr Thr Asn Gln Ala Thr
            100                 105                 110

Ala Leu Lys Glu Ala Leu Gln Pro Pro Ile His Leu Gly His Leu Pro
        115                 120                 125

Leu Gln Glu Gly Glu Leu Pro Leu Val Gln Gln Val Ala Pro Ser
    130                 135                 140

Asp Lys Pro Pro Lys Pro Glu Leu Pro Val Asp Phe Ala Asp Pro Gln
145                 150                 155                 160

Gly Pro Ser Leu Pro Gly Met Asp Phe Pro Asp Pro Gln Gly Pro Ser
                165                 170                 175

Leu Pro Gly Leu Asp Phe Ala Asp Pro Gln Gly Ser Thr Ile Phe Gln
            180                 185                 190

Ile Ala Arg
        195

<210> SEQ ID NO 37
<211> LENGTH: 21
<212> TYPE: DNA
<213> ORGANISM: Homo sapiens
<220> FEATURE:
<223> OTHER INFORMATION: PCR primer

<400> SEQUENCE: 37
tgaaggacct gatactgatc c                                              21

<210> SEQ ID NO 38
<211> LENGTH: 21
<212> TYPE: DNA
<213> ORGANISM: Homo sapiens
<220> FEATURE:
<223> OTHER INFORMATION: PCR primer

<400> SEQUENCE: 38
```

```
tgatttgctc caaaaggcac g                                            21
```

<210> SEQ ID NO 39
<211> LENGTH: 10
<212> TYPE: PRT
<213> ORGANISM: Homo sapiens
<220> FEATURE:
<223> OTHER INFORMATION: 10 aa from 1 to 10 in sequence 1

<400> SEQUENCE: 39

Ser Asp Lys Pro Pro Lys Pro Glu Leu Pro
1               5                   10

<210> SEQ ID NO 40
<211> LENGTH: 9
<212> TYPE: PRT
<213> ORGANISM: Homo sapiens
<220> FEATURE:
<223> OTHER INFORMATION: 9 aa from 1 to 9 in sequence 1

<400> SEQUENCE: 40

Ser Asp Lys Pro Pro Lys Pro Glu Leu
1               5

<210> SEQ ID NO 41
<211> LENGTH: 11
<212> TYPE: PRT
<213> ORGANISM: Homo sapiens
<220> FEATURE:
<223> OTHER INFORMATION: 11 aa from 3 to 14 in sequence 1

<400> SEQUENCE: 41

Lys Pro Pro Lys Pro Glu Leu Pro Val Asp Phe
1               5                   10

<210> SEQ ID NO 42
<211> LENGTH: 10
<212> TYPE: PRT
<213> ORGANISM: Homo sapiens
<220> FEATURE:
<223> OTHER INFORMATION: 10 aa from 141 to 150 in sequence 11

<400> SEQUENCE: 42

Val Ala Pro Ser Asp Lys Pro Pro Lys Pro
1               5                   10

<210> SEQ ID NO 43
<211> LENGTH: 8
<212> TYPE: PRT
<213> ORGANISM: Homo sapiens
<220> FEATURE:
<223> OTHER INFORMATION: 8 aa from 7 to 14 in sequence 1

<400> SEQUENCE: 43

Pro Glu Leu Pro Gly Val Asp Phe
1               5

<210> SEQ ID NO 44
<211> LENGTH: 16
<212> TYPE: PRT
<213> ORGANISM: Sus scrofa
<220> FEATURE:
<223> OTHER INFORMATION: 16 aa from 131 to 146 in sequence 10

<400> SEQUENCE: 44

Gln Val Glu Gly Pro Met Val Gln Gln Val Ala Pro Ser Glu Lys
1               5                   10                  15

```
<210> SEQ ID NO 45
<211> LENGTH: 21
<212> TYPE: DNA
<213> ORGANISM: Homo sapiens
<220> FEATURE:
<223> OTHER INFORMATION: osteopontin primer pair

<400> SEQUENCE: 45
tgacctctgt gaaaacagcg t                                              21

<210> SEQ ID NO 46
<211> LENGTH: 21
<212> TYPE: DNA
<213> ORGANISM: Homo sapiens
<220> FEATURE:
<223> OTHER INFORMATION: osteopontin primer pair

<400> SEQUENCE: 46
tgtacattgt gaagctgtga a                                              21

<210> SEQ ID NO 47
<211> LENGTH: 21
<212> TYPE: DNA
<213> ORGANISM: Homo sapiens
<220> FEATURE:
<223> OTHER INFORMATION: osteocalcin primer pair

<400> SEQUENCE: 47
ttgtgtccaa gcaggagggc a                                              21

<210> SEQ ID NO 48
<211> LENGTH: 21
<212> TYPE: DNA
<213> ORGANISM: Homo sapiens
<220> FEATURE:
<223> OTHER INFORMATION: osteocalcin primer pair

<400> SEQUENCE: 48
acatccatag ggctgggagg t                                              21

<210> SEQ ID NO 49
<211> LENGTH: 20
<212> TYPE: DNA
<213> ORGANISM: Homo sapiens
<220> FEATURE:
<223> OTHER INFORMATION: bone sialo protein primer pair

<400> SEQUENCE: 49
gcagaagtgg atgaaaacga                                                20

<210> SEQ ID NO 50
<211> LENGTH: 20
<212> TYPE: DNA
<213> ORGANISM: Homo sapiens
<220> FEATURE:
<223> OTHER INFORMATION: bone sialo protein primer pair

<400> SEQUENCE: 50
tggtggtagt attctgacca                                                20
```